United States Patent
Rozema et al.

(10) Patent No.: US 7,098,030 B2
(45) Date of Patent: *Aug. 29, 2006

(54) POLYAMPHOLYTES FOR DELIVERING POLYIONS TO A CELL

(75) Inventors: David B. Rozema, Madison, WI (US); Vladimir G. Budker, Middleton, WI (US); James E. Hagstrom, Middleton, WI (US); Vladimir Trubetskoy, Middleton, WI (US); Jon A. Wolff, Madison, WI (US); Sean D. Monahan, Madison, WI (US); Paul M. Slattum, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 50 days.

This patent is subject to a terminal disclaimer.

(21) Appl. No.: 10/899,509

(22) Filed: Jul. 26, 2004

(65) Prior Publication Data

US 2005/0037496 A1 Feb. 17, 2005

Related U.S. Application Data

(63) Continuation-in-part of application No. 10/095,682, filed on May 10, 2002, now Pat. No. 6,794,189, which is a continuation-in-part of application No. 09/753,990, filed on Jan. 2, 2001, now Pat. No. 6,383,811.

(60) Provisional application No. 60/174,132, filed on Dec. 31, 1999.

(51) Int. Cl.
C12N 15/88 (2006.01)

(52) U.S. Cl. .................. 435/450; 435/458; 514/44

(58) Field of Classification Search ............... None
See application file for complete search history.

(56) References Cited

U.S. PATENT DOCUMENTS

| | | | |
|---|---|---|---|
| 6,383,811 B1 * | 5/2002 | Wolff et al. | .............. 435/450 |
| 6,627,616 B1 | 9/2003 | Monahan et al. | |
| 6,794,189 B1 * | 9/2004 | Wolff et al. | .............. 435/458 |
| 6,867,196 B1 | 3/2005 | Wolff et al. | |

OTHER PUBLICATIONS

Asayama et al., "Synthesis of Novel Polyampholyte Comb-Type Copolymers Consisting of a Poly(L-lysine) Backbone and Hyaluronic Acid Side Chains for a DNA Carrier." Bioconjugate Chem 1998 vol. 9, No. 4; pp. 476-481.

Dash PR et al. "Factors Affecting Blood Clearance and In Vivo Distribution of Polyelectrolyte Complexes for Gene Delivery." Gene Therapy; 1999; vol. 6, pp. 643-650.

Elbashir et al. "Duplexes of 21-nucleotide RNAs mediate RNA interferencein cultured mammalian cells." Nature 2001 vol. 411 p. 494-498.

Murthy et al. "The Design and Synthesis of Polymers for Eukaryotic Membrane Disruption." Journal of Controlled Release; 1999; vol. 61; pp. 137-143.

Naganawa et al. "Synthetic Studies on Tautamycin synthesis of 2,3-disubstituted maleic anhydride segment." Tetrahedron 1994 vol. 50 No. 30 p. 8969-8982.

Netz R et al. "Complexation Behavior of Polyampholytes and Charged Objects." Macromolecules; 1998; vol. 51; pp. 5123-5141.

Ogris M et al. "PEGylated DNA/Transferrin-PEI Complexes: Reduced Interaction with Blood Components, Extended Circulation in Blood and Potential for Systemic Gene Delivery." Gene Therapy; 1996; vol. 6; pp. 595-605.

Plank C et al. "Activation of the Complement System by Synthetic DNA Complexes: A Potential Barrier for Intravenous Gene Delivery." Human Gene Therapy; Aug. 1, 1996; vol. 7; pp. 1437-1446.

Ross PC et al. "Lipoplex Size is a Major Determinant of In Vitro Lipofection Efficiency." Gene Therapy; 1999; vol. 6; pp. 651-659.

Sharp "RNA Interference-2001" Genes & Development 2001 vol. 15 p. 485-490.

Trubetskoy VS et al. "Layer-by-Layer Deposition of Oppositely Charged Polyelectrolytes on the Surface of Condensed DNA Particles." Nucleic Acids Research; 1999; vol. 27, No. 15; pp. 3090-3095.

Tushcl et al. "Targeted mRNA degradation by double-stranded RNA in vitro." Genes & Development 1999 vol. 13 p. 3191-3197.

Vitiello L et al. "Transfection of Cultured Myoblasts in High Serum Concentration with DODAC:DOPE Liposomes." Gene Therapy; 1998; vol. 5; pp. 1306-1313.

Wolfert MA et al. "Characterization of Vectors for Gene Therapy Formed by Self-Assembly of DNA with Synthetic Block Co-Polymers." Human Gene Therapy; Nov. 10, 1996; vol. 7; pp. 2123-2133.

Xu Y et al. "Mechanism of DNA Release from Cationic Liposome/DNA Complexes Used in Cell Transfection." Biochemistry; 1996; vol. 35, pp. 5616-5623.

* cited by examiner

Primary Examiner—James Ketter
(74) Attorney, Agent, or Firm—Mark K. Johnson; Kirk Ekena

(57) ABSTRACT

An polyampholyte is utilized in a condensed polynucleotide complex for purposes of nucleic acid delivery to a cell. The complex can be formed with an appropriate amount of positive and/or negative charge such that the resulting complex can be delivered to the extravascular space and may be further delivered to a cell.

20 Claims, 7 Drawing Sheets

POLYAMPHOLYTES FOR DELIVERING POLYIONS TO A CELL

CROSS-REFERENCE TO RELATED APPLICATIONS

This application is a continuation-in-part of application Ser. No. 10/095,682, filed May 10, 2002, now U.S. Pat. No. 6,794,189 which is a continuation-in-part of application Ser. No. 09/753,990 filed Jan. 02, 2001, now U.S. Pat. No. 6,383,811 which claims the benefit of U.S. Provisional Application No. 60/174,132 filed Dec. 31, 1999.

FIELD OF THE INVENTION

The invention relates to compounds and methods for use in biologic systems. More particularly, polyions are utilized for modifying the charge ("recharging") of particles, such as molecules, polymers, nucleic acids and genes for delivery to cells.

BACKGROUND

Polymers are used for drug delivery for a variety of therapeutic purposes. Polymers have also been used in research for delivery of nucleic acids (polynucleotides and oligonucleotides) to cells, the process is one step in reaching a goal of providing therapeutic processes. One of the several methods of nucleic acid delivery to the cells is the use of DNA-polyion complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective.

In terms of intravenous injection, polynucleotides must cross the endothelial barrier and reach the parenchymal cells of interest. The largest endothelia fenestrae (holes in the endothelial barrier) occur in the liver and have an average diameter from 75–150 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the target cells the DNA-polycation complex should be taken up by endocytosis.

Inhibition of gene expression can be affected by antisense polynucleotides, siRNA mediated RNA interference and ribozymes. RNA interference (RNAi) describes the phenomenon whereby the presence of double-stranded RNA (dsRNA) of sequence that is identical or highly similar to a target gene results in the degradation of messenger RNA (mRNA) transcribed from that target gene (Sharp 2001). It has been shown that dsRNAs <30 bp in length (short interfering RNAs or siRNAs) delivered to a cell, induce RNAi in mammalian cells in culture and in vivo (Tuschl et al. 1999; Elbashir et al. 2001). There are two major approaches to initiate siRNA-mediated silencing in mammalian cells. First, synthetic siRNA duplexes (typically between 19–30 base pairs in length) can be designed and generated against any gene the sequence of which is known. The synthetic siRNA then has to be delivered into the cytoplasm. Second, expression cassettes that will generate siRNA within the cell can be delivered to the cell. The two basic types of siRNA expression constructs code either for a hairpin RNA containing both the sense and the antisense sequence, separated by a loop region, or they contain two separate promoters driving the transcription of the sense and antisense RNA strand separately.

The intravascular delivery of nucleic acid has been shown to be highly effective for gene transfer into tissue in vivo (U.S. application Ser. No. 09/330,909, U.S. Pat. No. 6,627,616). Non-viral vectors are inherently safer than viral vectors, have a reduced immune response induction and have significantly lower cost of production. Furthermore, a much lower risk of transforming activity is associated with non-viral polynucleotides than with viruses.

Applicants have provided a process for delivering a compound across the endothelial barrier to the extravascular space and then to a cell.

SUMMARY

Described in a preferred embodiment is a process for enhancing delivery of a polyion to a cell, comprising the formation of a complex of polyampholyte and polyion. Then, delivering the complex into a cell. In a preferred embodiment, a process is described for delivering a polynucleotide to a cell, comprising: forming of a complex comprising a polyampholyte and a polynucleotide, and delivering the complex to a cell.

In another preferred embodiment, we describe a process for extravasation of a complex. The process comprises the formation of a complex of polyampholyte and polyion. Then, inserting the complex into a vessel and delivering the complex to an extravascular space.

In a preferred embodiment, polyampholyte compounds are described that form complexes with polynucleotides and enhance delivery of polynucleotides to mammalian cells. In a preferred embodiment, the present invention provides a wide variety of polyampholytes with labile groups that find use in polynucleotide delivery systems. The labile bond may be in the main-chain of the polyampholyte, in the side chain of the polyampholyte or between the main-chain of the polyampholyte and an ionic group or other functional group. The polynucleotide may be linked to the polyampholyte by a labile linkage. The labile groups are selected such that they undergo a chemical transformation when present in physiological conditions. The chemical transformation may be initiated by the addition of a compound to the cell or may occur spontaneously when introduced into intra-and/or extra-cellular environments (e.g., the lower pH environment present in an endosome or in the extracellular space surrounding tumors).

Reference is now made in detail to the preferred embodiments of the invention, examples of which are illustrated in the accompanying drawings.

DETAILED DESCRIPTION

Polyampholytes are copolyelectrolytes containing both polycations and polyanions in the same polymer. In aqueous solutions polyampholytes are known to precipitate near the isoelectric point and form micelle-like structures (globules) at the excess of either charge. Such globules maintain tendency to bind other charged macromolecules and particles (Netz et al. 1998).

In provisional application Ser. No. 60/093,153 we described gene transfer activity which can be substantially increased by adding polyanions to preformed DNA/polycation complexes (i.e. recharging). We confirmed the same phenomenon for cationic lipids (provisional application Ser. No. 60/150,160).

Figure 1:
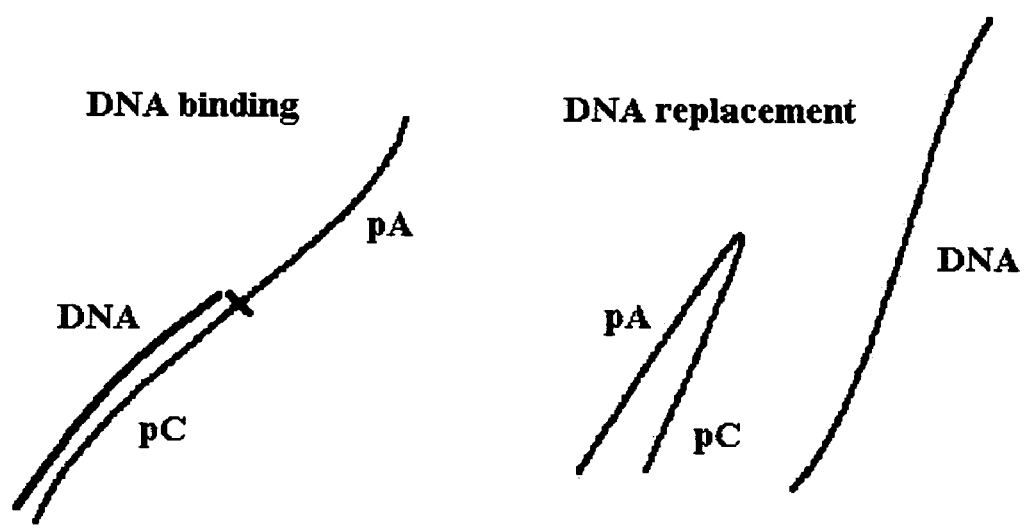
FIG. 1. DNA interactions with pC-pA block polyampholyte: binding (pA low charge density) and replacement (pA high charge density).

In this application we extend this principle into situations where DNA-binding polycation and polyanion are covalently linked into one polymer. Polyanions (polyanion=pA; polycation=pC) of higher charge density can displace DNA from its complex with polycation while pAs with lower charge density form triple complexes in which the complexes have a negative surface charge (Xu et al. 1996; Trubetskoy et al. 1999). Similarly, one can expect formation of DNA/polyampholyte complex in situations where a polyanion block ionically attached to a polyampholyte possesses a charge density lower than the charge density of the DNA molecule; A DNA molecule will be released from a complex with a polyampholyte when a polyanion block has a charge density higher than the DNA molecule (see FIG. 1). In the latter case, an internal pA-pC salt is formed.

It has previously been demonstrated that binding of negatively-charged serum components can significantly decrease gene transfer efficacy of DNA/polycation (DNA/pC) complexes in vivo (Vitiello et al. 1998; Ross et al. 1999). We have found that addition of polyanions to the point of near complex charge reversal drastically increases the efficacy of gene transfer mediated by DNA/pC complex upon i/v administration in mice (Provisional application Ser. No. 60/093,153). This improvement takes place due to protecting effect of pA which is situated as an outside shell on the triple complex and functions by inhibiting interactions of the complexes with serum proteins. We believe that gene transfer increase observed with DNA/polyampholyte complexes is based on the same phenomenon. The polyanion portion of polyampholyte being displaced from DNA/pC interaction can form an outside shell of negative charge and protect the complex from inhibiting interactions with serum proteins. The charge density of the pA is of primary importance. The higher charge density, the more effective is the protective effect against serum proteins.

In some cases a polyanionic block may be a natural protein or peptide used for cell targeting or other function. A polyanionic block can provide other functions too: for example, poly(propylacrylic acid) is known for pH-dependent membrane-disruptive function (Murthy etal. 1999).

To demonstrate the principle we synthesized two block polyampholytes of linear polyethyleneimine (lPEI) with 1) polymethacrylic acid (lPEI-pMAA, high charge density pA) and polyglutamic acid (lPEI-pGlu, low charge density pA) and prepared complexes with plasmid DNA (pClluc). We show that a covalent complex between pC and pA can substantially enhance gene transfer activity when compared to a non-polyampholyte mixture. We further describe the phenomena in the examples section of this application.

In this specification, the use of the term polyanion may refer to the anionic portion of the polyampholyte and the term polycation may refer to the cationic portion of the polyampholyte. Abbreviations: Poly-L-Lysine (PLL), succinic anhydride-PLL (SPLL), polymethacrylic acid, pMAA and polyaspartic acid, pAsp Polymers A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step. This classification description is more often used that the previous terminology of addition and condensation polymer.

Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that

Or the other approach is to have two difunctional monomers.

Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride,aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, or acid halide, p-nitrophenyl ester, o-nitrophenyl ester, pentachlorophenyl ester, pentafluorophenyl ester, carbonylimidazole, carbonyl pyridinium, or carbonyl dimethylaminopyridinium. In other terms when function A is an amine then function B can be acylating or alkylating agent or amination agent.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid {TNB} derivatives).

If functional group A is carboxylate then function B can be (but not restricted to) adiazoacetate or an amine in which a carbodiimide is used. Other additives may be utilized such as carbonyldiimidazole, dimethylamino pyridine (DMAP), N-hydroxysuccinimide or alcohol using carbodiimide and DMAP.

If functional group A is an hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used. If functional group A is an aldehyde or ketone then function B can be (but not restricted to) an hydrazine, hydrazide derivative, amine (to form a Schiff Base that may or may not be reduced by reducing agents such as NaCNBH$_3$) or hydroxyl compound to form a ketal or acetal.

Yet another approach is to have one bifunctional monomer so that A-A plus another agent yields -(A-A)-. If function A is a sulfhydryl group then it can be converted to disulfide bonds by oxidizing agents such as iodine (I$_2$) or NaIO$_4$ (sodium periodate), or oxygen (O$_2$).

Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid {TNB} derivatives) can also be used to catalyze disulfide bond formation. Functional group A or B in any of the above examples could also be a photoreactive group such as aryl azide (including halogenated aryl azide), diazo, benzophenone, alkyne or diazirine derivative.

Reactions of the amine, hydroxyl, sulfhydryl, carboxylate groups yield chemical bonds that are described as amide, amidine, disulfide, ethers, esters, enamine, imine, urea, isothiourea, isourea, sulfonamide, carbamate, alkylamine bond (secondaryamine), carbon-nitrogen single bonds in which the carbon contains a hydroxyl group, thioether, diol, hydrazone, diazo, or sulfone.

If functional group A is an aldehyde or ketone then function B can be (but not restricted to) an hydrazine, hydrazide derivative, amine (to form a Schiff Base that may or may not be reduced by reducing agents such as NaCNBH$_3$) or hydroxyl compound to form a ketal or acetal.

Yet another approach is to have one difunctional monomer so that

A-A plus another agent yields -(A-A)-.

If function A is a sulfhydryl group then it can be converted to disulfide bonds by oxidizing agents such as iodine (I$_2$) or NaIO$_4$ (sodium periodate), or oxygen (O$_2$). Function A can also be an amine that is converted to a sulfhydryl group by reaction with 2-iminothiolate (Traut's reagent) which then undergoes oxidation and disulfide formation. Disulfide derivatives (such as a pyridyl disulfide or 5-thio-2-nitrobenzoic acid {TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thioether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methaacrylamide groups can undergo chain reaction which can be radical, anionic, or cationic. Chain polymerization can also be accomplished by cycle or ring opening polymerization. Several different types of free radical initiators could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrozyine, heterocycles (like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyl-dipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties carbohydrates; polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bond. Hydrocarbons are hydrophobic groups. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups such groups are used for targeting the polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Peptide refers to a linear series of amino acid residues connected to one another by peptide bonds between the alpha-amino group and carboxyl group of contiguous amino acid residues. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Reporter or marker molecules are compounds that can be easily detected. Typically they are fluorescent compounds such as fluorescein, rhodamine, texas red, CY-5, CY-3 or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

In a preferred embodiment, a chemical reaction can be used to attach a signal to a nucleic acid complex. The signal is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The signal can be a protein, peptide, lipid, steroid, sugar, carbohydrate, nucleic acid or synthetic compound. The signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, Golgi apparatus, trans Golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin Al and the ER-retaining signal (KDEL sequence), viral components such as influenza virus hemagglutinin subunit HA-2 peptides and other types of amphipathic peptides.

Cellular receptor signals are any signal that enhances the association of the gene or particle with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Extravascular means outside of a vessel such as a blood vessel. Extravascular space means an area outside of a vessel. Space may contain biological matter such as cells and does not imply empty space.

Extravasation means the escape of material such as compounds and complexes from the vessel into which it is introduced into the parenchymal tissue or body cavity.

The process of delivering a polynucleotide to a cell has been commonly termed transfection or the process of transfecting and also it has been termed transformation. The polynucleotide could be used to produce a change in a cell that can be therapeutic. The delivery of polynucleotides or genetic material for therapeutic and research purposes is commonly called gene therapy. The polynucleotides or genetic material being delivered are generally mixed with transfection reagents prior to delivery.

The polyampholyte complex is a complex having the potential to react with biological components. More particularly, polyampholyte complexes utilized in this specification are designed to change the natural processes associated with a living cell. For purposes of this specification, a cellular natural process is a process that is associated with a cell before delivery of a polyampholyte complex. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, and nucleic acids are examples that can be components of polyampholyte complexes.

The term polynucleotide is a term of art that refers to a polymer containing at least two nucleotides. Nucleotides contain a sugar deoxyribose (DNA) or ribose (RNA), a base, and a phosphate group. Nucleotides are linked together through the phosphate groups. Bases include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A polynucleotide containing fewer than 80 monomeric units is often called an oligonucleotide. The term nucleic acid includes deoxyribonucleic acid (DNA) and ribonucleic acid (RNA). DNA may be in the form of anti-sense, plasmid DNA, parts of a plasmid DNA, vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups. Anti-sense is a polynucleotide that interferes with the function of DNA and/or RNA. This may result in suppression of expression. Natural nucleic acids have a phosphate backbone, artificial nucleic acids may contain other types of backbones, nucleotides, or bases. These include PNAs (peptide nucleic acids), phosphothionates, and other variants of the phosphate backbone of native nucleic acids. In addition, DNA and RNA may be single, double, triple, or quadruple stranded. Expression cassette refers to a natural or recombinantly produced polynucleotide molecule which is capable of expressing protein(s). A DNA expression cassette typically includes a promoter (allowing transcription initiation), and a sequence encoding one or more proteins. Optionally, the expression cassette may include transcriptional enhancers, non-coding sequences, splicing signals, transcription termination signals, and poly-adenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15–50 base pairs and preferably 19–25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

The term naked polynucleotides indicates that the polynucleotides are not associated with a transfection reagent or other delivery vehicle that is required for the polynucleotide to be delivered to the cardiac muscle cell. A transfection reagent is a compound or compounds used in the prior art that bind(s) to or complex(es) with oligonucleotides and polynucleotides, and mediates their entry into cells. The transfection reagent also mediates the binding and internalization of oligonucleotides and polynucleotides into cells. Examples of transfection reagents include cationic liposomes and lipids, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents, while small polycations like spermine may be ineffective. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA. Polyethylenimine, which facilitates gene expression without additional treatments, probably disrupts endosomal function itself.

Other vehicles are also used, in the prior art, to transfer genes into cells. These include complexing the polynucleotides on particles that are then accelerated into the cell. This is termed biolistic or gun techniques. Other methods include electroporation, in which a device is used to give an electric charge to cells. The charge increases the permeability of the cell. Charge density is the term used to describe the electrical charge per unit area, for example, on a polymer.

Ionic (electrostatic) interactions are the non-covalent association of two or more substances due to attractive forces between positive and negative charges, or partial positive and partial negative charges.

Condensed Nucleic Acids: Condensing a polymer means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism.

A delivered polymer can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Condensed nucleic acids may be delivered intravasculary, intrarterially, intravenously, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. Delivered means that the polynucleotide becomes associated with the cell. The polynucleotide can be on the membrane of the cell or inside the cytoplasm, nucleus, or other organelle of the cell.

An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

An administration route involving the mucosal membranes is meant to include nasal, bronchial, inhalation into the lungs, or via the eyes.

Recharging Condensed Nucleic Acids

Polyions for gene therapy and gene therapy research can involve anionic systems as well as charge neutral or charge-positive systems. The ionic polymer can be utilized in recharging (another layer having a different charge) the condensed polynucleotide complex. The resulting recharged complex can be formed with an appropriate amount of charge such that the resulting complex has a net negative, positive or neutral charge. The interaction between the polycation and the polyanion can be ionic, can involve the ionic interaction of the two polymer layers with shared cations, or can be crosslinked between cationic and anionic sites with a crosslinking system (including cleavable crosslinking systems, such as those containing disulfide bonds). The interaction between the charges located on the two polymer layers can be influenced with the use of added ions to the system. With the appropriate choice of ion, the layers can be made to disassociate from one another as the ion diffuses from the complex into the cell in which the concentration of the ion is low (use of an ion gradient).

Electrostatic complexes between water-soluble polyelectrolytes have been studied widely in recent ears. Complexes containing DNA as a polyanionic constituent only recently came to the attention because of their potential use in gene therapy applications such as non-viral gene transfer preparations (polyplexes) for particle delivery to a cell. Strong polyelectrolytes, polyanion/polycation complexes, are usually formed at a 1:1 charge stoichiometrically. A charge ratio 1:1 complex between DNA and Poly-L-Lysine (PLL) also has been demonstrated in the prior art.

Polyanions effectively enhance the gene delivery/gene expression capabilities of all major classes of polycation gene delivery reagents. In that regard, we disclose the formation of negatively charged tertiary complexes containing nucleic acid, PLL, and succinic anhydride-PLL (SPLL) complexes. SPLL is added to a cationic nucleic acid/PLL complex in solution. Nucleic acid at the core of such complexes remains condensed, in the form of particles ~50 nm in diameter. DNA and PLL binds SPLL in 1:1:1 complex with SPLL providing a net negative charge to the entire complex. Such small negatively charged particles are useful for non-viral gene transfer applications.

One of the advantages that flow from recharging DNA particles is reducing their non-specific interactions with cells and serum proteins ((Wolfert et al. 1996; Dash et al. 1999; Plank et al. 1996; Ogris et al. 1999).

A wide a variety of polyanions can be used to recharge the DNA/polycation particles. They include (but not restricted to): Any water-soluble polyanion can be used for recharging purposes including succinylated PLL, succinylated PEI (branched), polyglutamic acid, polyaspartic acid, polyacrylic acid, polymethacrylic acid, polyethylacrylic acid, polypropylacrylic acid, polybutylacrylic acid, polymaleic acid, dextran sulfate, heparin, hyaluronic acid, polysulfates, polysulfonates, polyvinyl phosphoric acid, polyvinyl phosphonic acid, copolymers of polymaleic acid, polyhydroxybutyric acid, acidic polycarbohydrates, DNA, RNA, negatively charged proteins, pegylated derivatives of above polyanions, pegylated derivatives carrying specific ligands, block and graft copolymers of polyanions and any hydrophilic polymers (PEG, poly(vinylpyrrolidone), poly(acrylamide), etc).

DNA condensation assays based on the effect of concentration-dependent self-quenching of covalently-bound fluorophores upon DNA collapse indicated essentially the same phenomenon described in the prior art. Polyanions with high charge density (polymethacrylic acid, pMAA and polyaspartic acid, pAsp) were able to decondense DNA prior to those that complexed with PLL while polyanions with lower charge density (polyglutamic acid, pGlu, SPLL) failed to decondense DNA. Together with z-potential measurements, these data represent support for the presence of negatively charged condensed DNA particles. These particles are approximately 50 nm in diameter in low salt buffer as measured by atomic force microscopy which revealed particles of spheroid morphology. This places them very close in size to binary DNA/PLL particles. Particles prepared using various pC/pA polyampholytes can be used to form similar condensed DNA particles.

In another preferred embodiment, the polyanion can be covalently attached to the polycation using a variety of chemical reactions without the use of crosslinker. The polyanion can contain reactive groups that covalently attach to groups on the polycation. This results in the formation of a polyampholyte The types of reactions are similar to those discussed above in the section on step polymerization.

In another preferred embodiment the attachment of the recharged complex can be enhanced by using chelators and crown ethers, preferably polymeric.

In one preferred embodiment the DNA/polycation complexes are initially formed by adding only a small excess of polycation to nucleic acid (in charge ratio which is defined as ratio of polycation total charge to polyanion total charge at given pH). The charge ratio of polycation to nucleic acid charge could be less than 2, less than 1.7, less than 1.5 or even less than 1.3. This would be preferably done in low ionic strength solution so as to avoid the complexes from flocculation. Low ionic strength solution means solution with total monovalent salt concentration less than 50 mM. Then the polyanion is added to the mixture and only a small amount of blank particles are formed. Blank particles are particles that contain only polycation and polyanion and no nucleic acid.

In another preferred embodiment, the polycation is added to the nucleic acid in charge excess but the excess polycation that is not in complex with the nuclei acid is removed by purificaton. Purification means removing of charged polymer using centrifugation, dialysis, chromatography, electrophoresis, precipitation, extraction.

Yet in another preferred embodiment a ultracentrifugation procedure (termed centrifugation step) is used to reduce the amount of excess polycation, polyanion, or blank particles. The method is based on the phenomenon that only dense DNA-containing particles can be centrifuged through 10% sucrose solution at 25,000 g. After centrifugation purified complex is at the bottom of the tube while excess of polyanion and blank particles stay on top. In modification of this experiment 40% solution of metrizamide can be used as a cushion to collect purified DNA/polycation/polyanion complex on the boundary for easy retrieval.

The attachment of the polyanion to the DNA/polycation complex enhance stability but can also enable a ligand or signal to be attached to the DNA particle. This is accomplished by attaching the ligand or signal to the polyanion which in turn is attached to the DNA particle. A dialysis step or centifugation step can be used to reduce the amount of free polyanion containing a ligand or signal that is in solution and not complexed with the DNA particle. One approach is to replace the free, uncomplexed polyanion containing a ligand or signal with free polyanion that does not contain a ligand or signal.

Yet in another preferred embodiment a polyanion used for charge reversal is modified with neutral hydrophilic polymer for steric stabilization of the whole complex. The complex formation of DNA with pegylated polycations results in substantial stabilization of the complexes towards salt- and serum-induced flocculation (Wolfert et al. 1996, Ogris et al. 1999). We have demonstrated that modification of polyanion in triple complex also significantly enhances salt and serum stability.

In another preferred embodiment a polyanion used for charge reversal is cleavable. One can imagine two ways to design a cleavable polyion: 1. A polyion cleavable in backbone, 2. A polyion cleavable in side chain. First scenario would comprise monomers linked by labile bonds such as disulfide, diols, diazo, ester, sulfone, acetal, ketal, enol ether, enol ester, imine and enamine bonds. Second scenario would involve reactive groups (i.e. electrophiles and nucleophiles) in close proximity so that reaction between them is rapid. Examples include having corboxylic acid derivatives (acids, esters and amides) and alcohols, thiols, carboxylic acids or amines in the same molecule reacting together to make esters, thiol esters, anhydrides or amides. In one specific preferred embodiment the polyion contains an ester acid such as citraconnic acid, or dimethylmaleyl acid that is connected to a carboxylic, alcohol, or amine group on the polyion.

Cleavable means that a chemical bond between atoms is broken. Labile also means that a chemical bond between atoms is breakable. Crosslinking refers to the chemical attachment of two or more molecules with a bifunctional reagent. A bifunctional reagent is a molecule with two reactive ends. The reactive ends can be identical as in a homobifunctional molecule, or different as in a heterobifucnctional molecule.

An important consideration in selecting labile bonds for use in cellular delivery systems is the kinetics of bond cleavage upon exposure of the bond to acidic pH. The kinetics of endosome acidification and maturation of the endosome to a lysosome are very rapid compared to the rates of cleavage for most of the acid-labile bonds reported in the literature. Once endocytosis occurs, the pH drops from the extracellular pH (about 7.4) to pH about 5 in roughly 10 min. Endosomal contents are quickly exposed to active lysosomal enzymes and degradation of the molecule to be delivered may occur. Therefore, bonds that are cleaved in within minutes in the pH range 5–7 are preferred.

A well-studied pH-labile bond is the maleamate bond, which is derived from the reaction of an amine and a maleic anhydride or maleic anhydride derivative. The rate of maleamate cleavage is dependent upon the structure of the maleic anhydride used to form the maleamate. In general, disubstituted maleamates are more labile than monosubstituted maleamates, which are more labile than unsubstituted maleamates. The monosubstituted maleamates are the most studied members of this family, and have half-lives of hours at pH<5. According to literature, disubstitution of the maleamate results in about two orders of magnitude increase in the rate of cleavage. We have found that the disubstituted maleamate bond derived from dimethylmaleic anhydride has a half-life of about 2 min at pH 5. This rate is on the same order as endosome maturation. In contrast, we have found that monosubstituted maleamate bonds derived from methylmaleic anhydride have a half-life of cleavage of about 300 min (5 hours) at pH 5. To increase charge and solubility, derivatives of dimethyl maleic anhydrides, such as 2-Propionic-3-Methylmaleic Anhydride (Naganawa et al. 1994; Carboxylated DimethylMaleic anhydride or CDM) may be used. Modification of a polymer with a CDM maleic anhydride derivative can reversibly convert positive charges on the polymer to negatively charged carboxyl groups. Thus, a polycation can be converted to a polyanion.

EXAMPLES

Example 1

Synthesis of lPEI-pMAA and lPEI-pGlu Complexes

The following polyions were used for the reaction: lPEI (MW=25 kDa, Polysciences), pMAA (MW=9.5 kDa, Aldrich), pGlu (MW=49 kDa, Sigma). For analytical purposes pAs covalently labeled with rhodamine-ethylenediamine (Molecular Probes) were used for these reactions (degree of carboxy group modification <2%). Absorbance of the pAs was used to trace pAs and conjugates during size exclusion chromatography. PMAA (or pGlu, 1 mg in 100 µL water) was activated in in the presence of water-soluble carbidiimide (EDC, 100 µg) and N-hydroxysulfosuccinimide (100 µg) for 10 min at pH 5.5. Activated pMAA was added to the solution of lPEI (2 mg in 200 µL of 25 mM HEPES, pH 8.0) and incubated for 1 h at room temperature.

Example 2

Figure 2:
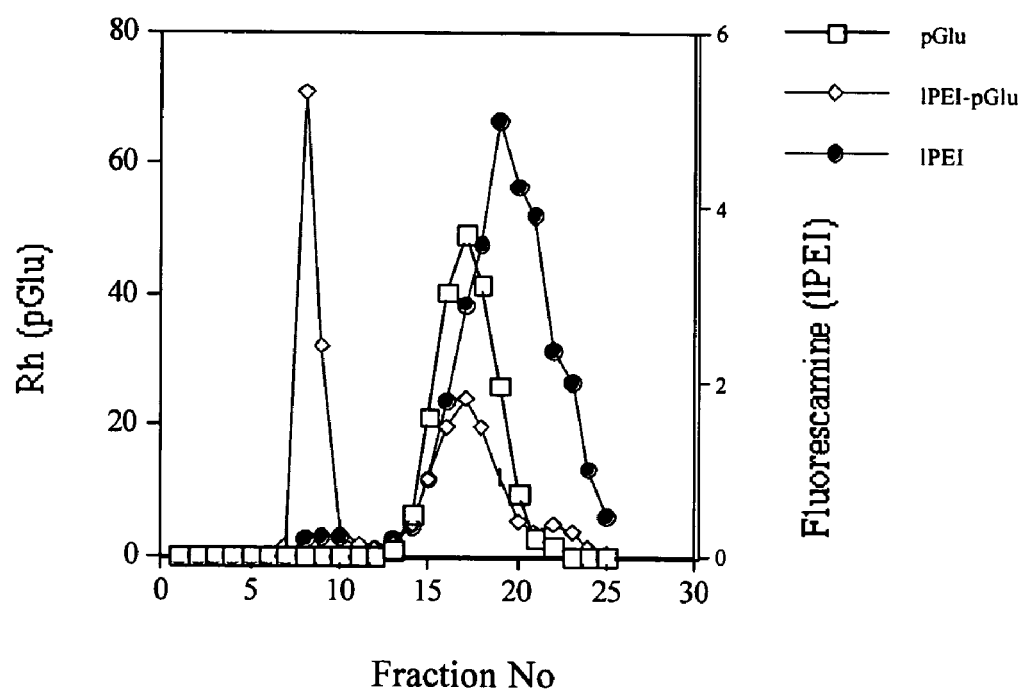
FIG. 2. Isolation of lPEI-pGlu polyampholyte using Example 1 reaction mixture.

Separation of lPEI-pMAA and lPEI-pGlu Reaction Mixtures Using Sepharose 4B-CL Column in 1.5 MNaCl After the reaction completion equal volume of 3 M NaCl solution was added to the part of the reaction mixture. This part (0.5 ml) was passes through the Sepharose 4B-CL column (1×25 cm) equlibrated in 1.5 M NaCl. Volume of the fractions collected was 1 ml. Rhodamine fluorescence was measured in each fraction. Linear PEI was measured using fluorescamine reaction. The amount of polyampholyte in the lPEI-pGlu reaction mixture is about 50% (see FIG. 2).

Example 3

HUH7 Mouse Liver Cell Transfection Using DNA/lPEI-pA Polyampholyte Mixtures

Figure 3:
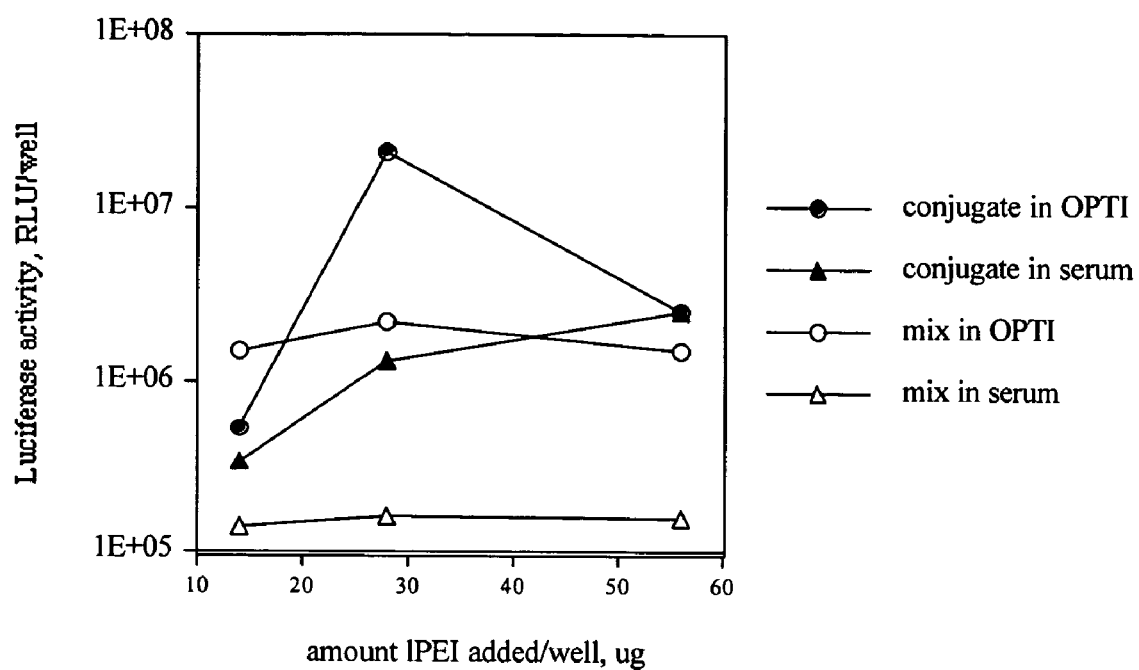
FIG. 3. Transfection of HUH7 cells using lPEI-pGlu polyampholyte using Example 1 reaction mixture.
Figure 4:
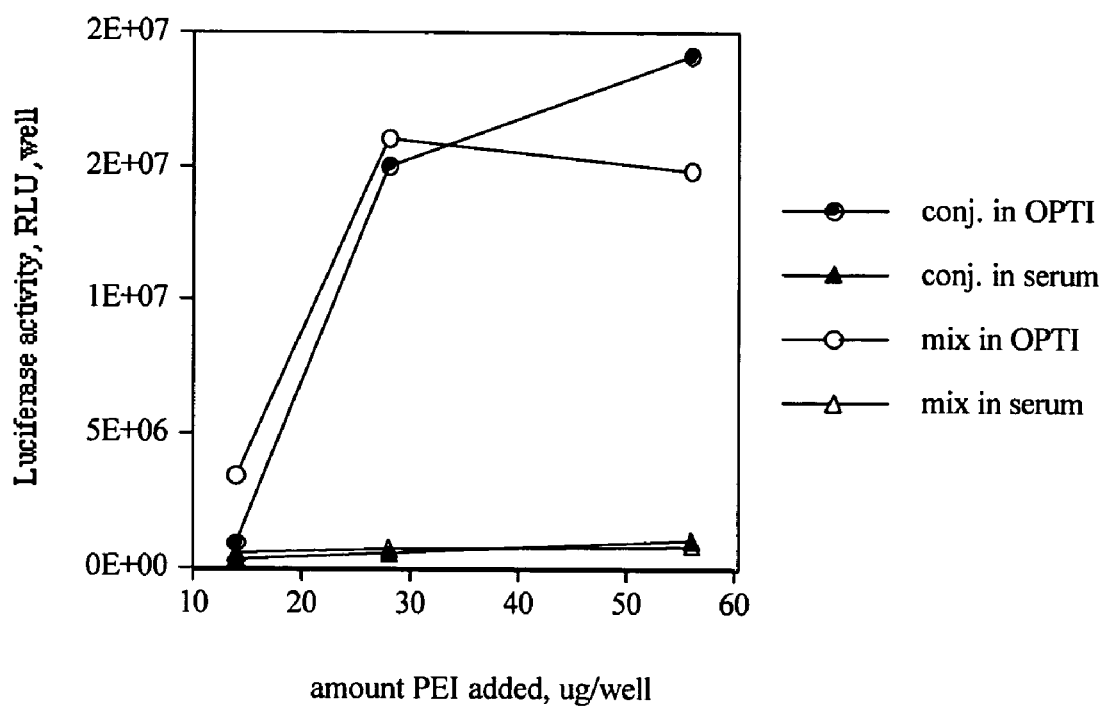
FIG. 4. Transfection of HUH7 cells using lPEI-pMAA polyampholyte using Example 1 reaction mixture.

Part of the polyampholyte reaction mixtures lPEI-pMAA and lPEI-pGlu were used to transfect HUH7 cells in culture. Non-covalent mixtures of lPEI with pMAA and pGlu mixed in the same ratios as for conjugates were used as the controls. Luciferase-encoded plasmid pCIluc (2 µg per 35 mm well) was used for transfection in OPTIMEM (cell medium) and OPTIMEM supplemented with 10% bovine serum. Amount of polyampholyte added is indicated on the basis of lPEI content. Results of this experiment are shown on FIGS. 3 and 4. There is a strong enhancement of transfection for polyampholytes in case of weaker pA conjugate (lPEI-pGlu, FIG. 3.) and almost no difference in transfection abilities of conjugates and mixtures for stronger pA (lPEI-pMAA, FIG. 4) in accordance to FIG. 1 scheme.

Example 4

Optimized Synthesis of lPEI-pGlu Polyampholyte

Figure 5:
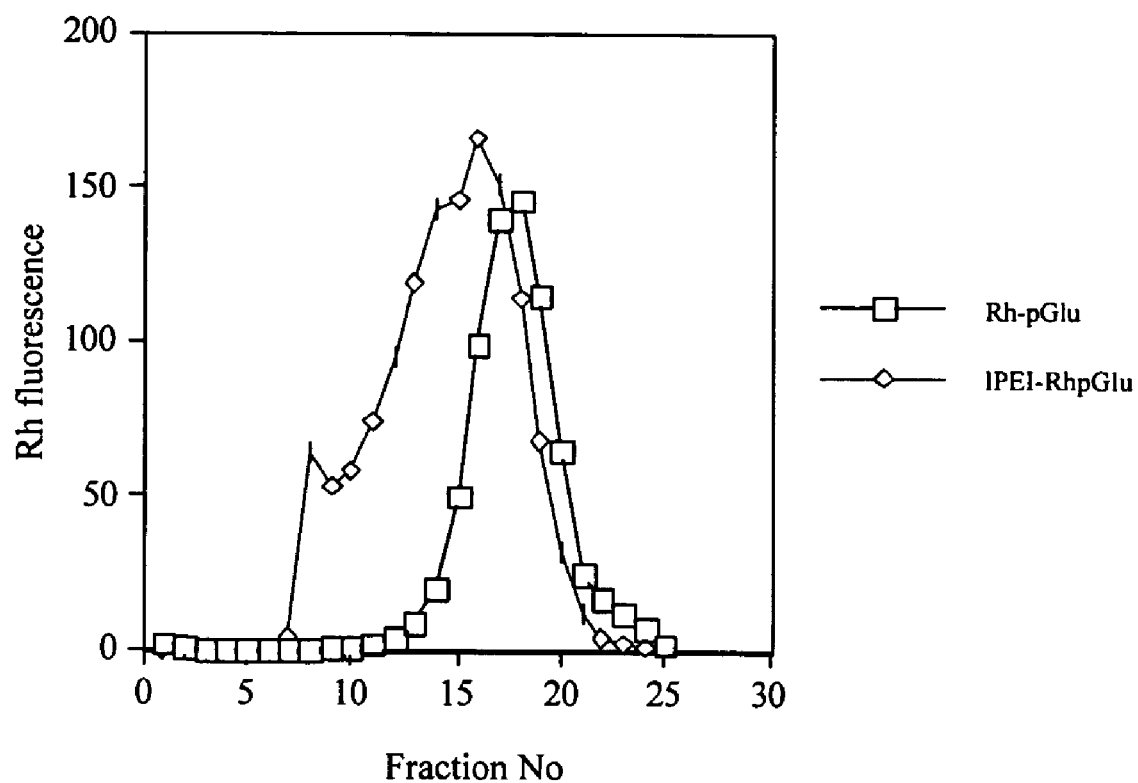
FIG. 5. Sepharose 4B-CL chromatography of rhodamine-labeled pGlu and lPEI-pGlu polyampholyte.

Rhodamine-labeled polyglutamic acid (pGlu, 150 uL, 20 mg/ml, titrated to pH 5.0) was activated with water-soluble [3'-(dimethylaminopropyl)-3-ethyl]carbodiimide (EDC, 15 ul, 100 mg/ml in DMSO) and sulfosuccinimide (SNHS, 15 um, 100 mg/ml in water) for 10 min. Then linear PEI (lPEI, 150 µl, 20 mg/ml) was added to the mixture, pH was adjusted to 8.0 and the mixture was allowed to stand for 2 hrs at room temperature. After this the mixture was passed through Sepharose 4B-CL column (1×20 cm) equilibrated with 1.5 M NaCl solution (FIG. 5). Rhodamine fluorescence was measured in each fraction. Fractions 10–14 were pooled, dialysed against water and freeze-dried to yield purified polyampholyte.

Example 5

Figure 6:
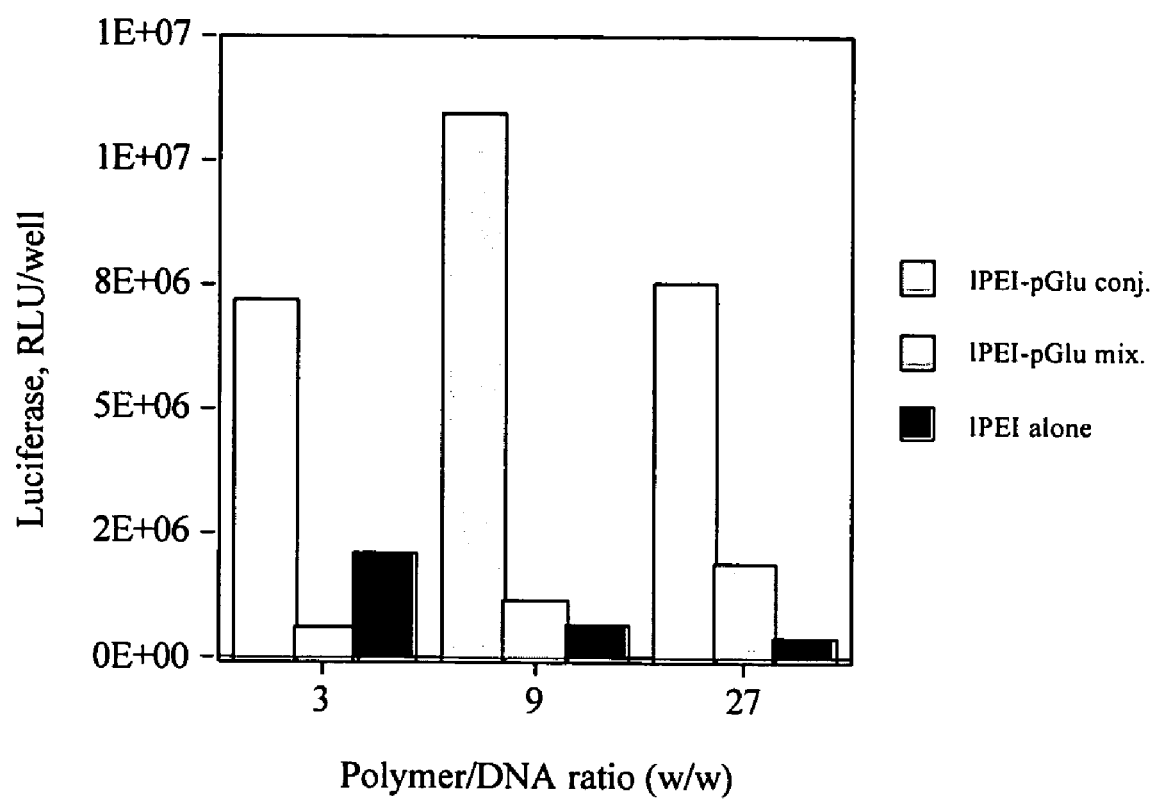
FIG. 6. Luciferase expression in HUH7 cells in vitro in 100% bovine serum aided by covalent lPEI-pGlu polyampholyte as compared to lPEI-pGlu non-covalent mixture and lPEI alone.

HUH7 Mouse Liver Cell Transfection Using DNA/lPEI-pA Polyampholyte Mixtures in the Presence of 100% Serum The luciferase encoding plasmid pCILuc was used for in vitro and in vivo gene transfer experiments. The DNA/polymer complexes were formed in 5 mM HEPES, 50 mM NaCl, 0.29 M glucose, pH 7.5 at DNA concentration of 50 µg/ml. HUH7 mouse liver cells were subconfluently seeded in 12-well plates. The complexes (1 µg of DNA) were added directly to 1 ml of 100% bovine serum into each well and incubated with cells for 4 hrs. After this step the cells were washed with OPTI-MEM media, supplemented with fresh media and maintained for additional 48 hrs. After this period of time the cells were harvested, lysed and processed for luciferase expression measurements. Non-covalent mixture of lPEI and pGlu as well as lPEI alone were used a controls in this experiment (FIG. 6). As one can see, the covalent conjugate of lPEI and pGlu gave significantly higher gene transfer activity in high range of polymer/DNA ratios as compared to controls.

Example 6

Synthesis of Branched PEI (brPEI)—pGlu and brPEI-pAsp Polyampholytes

Polyglutamic acid (pGlu, 2.28 mg in 172 µl of water, pH 5.5) or polyaspartic acid (pAsp, 2 mg in 172 µl of water) were activated in the presence of 100 ug of EDC and SNHS each for 10 min at room temperature. BrPEI (4 mg) and 2.5 M Na Cl (0.5 ml) solutions were added to the activated polyanion. The reaction mixture was allowed to incubate for 5 h at RT. Resulting brPEI-based polyampholytes were dialyzed against water and freeze-dried.

Example 7

In vivo Gene Transfer Activity of DNA/polyampholyte Complexes Prepared from Branched PEI BrPEI-pGlu and brPEI-pAsp polyampholytes were mixed with DNA at different w/w ratios in 5 mM HEPES, 0.29 M glucose, pH 7.5 at the DNA concentration of 0.2 mg/ml. The complexes (0.25 ml per animal) were intravenously injected into mouse tail vein (2 animals per group). The animals were sacrificed 24 hrs after injection and the lungs were processed for luciferase activity. The results of in vivo gene transfer are presented in the table below:

TABLE 1

Luciferase activity (RLU) in lungs after intravenous administration of DNA/brPEI-based polyampholytes in mice. Each animal received 50 ug of DNA in 0.25 ml of isotonic glucose solution. There were 2 animals per group. Survival of all animals in the group marked as non-toxic.

| Ratio (w/w) | DNA/brPEI | DNA/brPEI-pAsp | DNA/brPEI-pGlu |
|---|---|---|---|
| 1:1 | 600, non-toxic | 88,000, non-toxic | 34,000, non-toxic |
| 1:2 | All died | 600,000, one died | 3,900,000, non-toxic |
| 1:3 | n/a | n/a | 4,800,000, one died |

As one can see, complexing DNA with brPEI-based polyampholytes results in effective preparations for DNA delivery to parenchymal cells. BrPEI alone is ineffective at low weight ratios and toxic at higher ratios. Covalent conjugation of polyanions results in significant increase in gene transfer efficacy in lungs accompanying with reduction of toxicity.

Example 8

Delivery of an Active siRNA to a Cell Using an siRNA-polycation Polyampholyte

A. Synthesis of polycation DW561: 2-Vinyloxy Ethyl Phthalimide (1 g, 4.6 mmol) was added to an oven dried round bottom flask under a blanket of nitrogen in anhydrous dichloromethane. To this solution was added butyl vinyl ether (0.460 g, 4.6 mmol). The solution was then brought to −78° C., $BF_3.OEt_2$ (0.065 g, 0.46 mmol) was added and the reaction was allowed to proceed for 2 hours at −78° C. The polymerization was stopped by the addition of a 50/50 mixture of ammonium hydroxide in methanol. The solvents were then removed by rotary evaporation. The polymer was then dissolved in 30 mL of 1,4-dioxane/methanol (2/1). To this solution was added hydrazine (0.147 g, 46 mmol) and the mixture was heated to reflux for 3 hours. The solvents were then removed by rotary evaporation. The resulting solid was brought up in 20 mL of 0.5 M HCl, refluxed for 15 minutes, diluted with 20 mL distilled water, and refluxed for an additional hour. This solution was then neutralized with NaOH, cooled to room temperature, transferred to 3,500 molecular weight cutoff cellulose tubing, dialyzed for 24 h (2×20L) against distilled water and freeze dried.

B. Modification of DW561 with activated disulfide groups: 200 μg of polymer DW561 in 200 μl 5 mM HEPES buffer pH 7.5 was reacted with 10 μg of N-Succinimidyl 3-[2-pyridyldithio]-propionamido (SPDP) reagent (Pierce) to attach an activated disulfide pyridyldithio group to the polymer. Enough SPDP was used to modify 5% of the DW561 amines if the 100% of the SPDP reacted with the polymer. The polymer was used without purification.

C. Attachment of siRNA to polycation DW561 and delivery of small interfering RNA: 1.25 μM of siRNA targeted against luciferase modified on the sense strand at the 5' end with a thiol group was complexed with 25 μg of DW561-PDP, forming covalent linkages between the thiol on the anionic siRNA and the PDP groups on the polycation. Unreacted siRNA complexed with the siRNA-DW561 polyampholyte and was not removed prior to adding the polyampholyte to cells. As a control, we compared the inhibition of luciferase from these particles to inhibition by siRNA delivered by the commercially available siRNA transfection reagent TransIT-TKO. The polyampholytes were added to a mouse hepatocyte cell line (Hepa) that stably expresses the luciferase gene. The siRNA-DW561 polyampholytes were added to the cells such that monomer siRNA concentration was 50 nM. After 24–48 hours, luciferase activity in the cells was measured.

| Sample | Relative Luciferase Expression |
|---|---|
| no siRNA | 100% |
| TransIT-TKO | 6% |
| siRNA-DW561 polyampholyte | 40% |

D. Modification of siRNA-DW561 polyampholyte with CDM: 1.25 μM of siRNA targeted against luciferase and was modified on the sense strand at the 5' end with a thiol group was complexed with 25 μg of DW561. After allowing the polymer and siRNA to conjugate for 2 h, the conjugate was reacted with 0.25 or 0.5 molar equivalents (CDM to amines of unmodified DW561) of CDM. The siRNA-DW561-CDM polyampholytes were added to the cells such that monomer siRNA concentration was 50 nM. After 24–48 h, luciferase activity in the cells was measured.

| Sample | Relative Luciferase Expression |
|---|---|
| no siRNA | 100% |
| siRNA-DW561-CDM(0.25) | 31% |
| siRNA-DW561-CDM(0.5) | 15% |

Example 9

Inhibition of Gene Expression in Lung Following Delivery of siRNA Using siRNA/brPEI-pAA Polyampholytes In this example we show that polyampholyte complexes can be used for in vivo cellular delivery of siRNA. The delivered siRNA inhibits gene expression in a sequence-specific manner. To demonstrate functional delivery of siRNA to lung, mice were first transfected with two distinct luciferase genes encoding either firefly and renilla luciferase using recharged plasmid DNA/lPEI/polypropylacrylic acid complexes. Plasmid DNA complexes were prepared by combining 49.5 μg pMIR116 (firefly luciferase plasmid vector) and 0.5 μg pMIR122 (renilla luciferase plasmid vector) with 200 μg linear-PEI in 5 mM HEPES pH 7.5/290 mM glucose. 50 μg polyacrylic acid was then added to recharge the complexes. The complexes, in a total volume of 250 μl, were then injected into the tail vain of each mouse. Two hours after injection of recharged DNA complexes, mice were injected via tail vain with 250 μl injection solution containing siRNA/polyampholytes complexes made with 50 μg firefly luciferase specific siRNA-luc+.

siRNA: Single-stranded, gene-specific sense and antisense RNA oligomers with overhanging 3' deoxynucleotides were prepared and purified by PAGE (Dharmacon, LaFayette, CO). The two complementary oligonucleotides, 40 μM each, were annealed in 250 μl 100 mM NaCl/50 mM Tris-HCl, pH 8.0 buffer by heating to 94° C. for 2 minutes, cooling to 90° C. for 1 minute, then cooling to 20° C. at a rate of 1° C. per minute. The resulting siRNA was stored at −20° C. prior to use. The sense oligonucleotide, with identity to the luc+ gene in pGL-3-control, had the sequence: 5'-rCrUrUrArCrGrCrUrGrArGrUrArCrUrU-rCrGrATT-3' (SEQ ID 1), corresponding to positions 155–173 of the luc+reading frame. The antisense oligonucleotide, with identity to the luc+ gene in pGL-3-control, had the sequence: 5'-rUrCrGrArArGrUrArCrUrCrArGrCrGrUrArArGTT-3' (SEQ ID 2) corresponding to positions 173–155 of the luc+ reading frame in the antisense direction. The letter "r" preceding a nucleotide indicates that the nucleotide is a ribonucleotide. The annealed oligonucleotides containing luc+ coding sequence are referred to as siRNA-luc+. Polyampholyte: Branched PEI-pAA polyampholyte was prepared as described below.

Injection solution contained siRNA complexed with varying amounts of polyampholytes. Complexes were prepared using 50 μg siRNA and the indicated amount of brPEI-poly (aspartic acid) polyampholyte. Polyampholyte was mixed with siRNA in 5 mM HEPES pH 7.5/290 mM glucose, 250 μl total volume, and injected within 1 h of complex preparation. Controls included siRNA/brPEI complexes and siRNA/brPEI/pAsp complexes. 24 h after siRNA complex injection, lung tissue was harvested and assayed for luciferase activity using the Promega Dual Luciferase Kit (Promega) and a Lumat LB 9507 luminometer (EG&G Berthold, Bad-Wildbad, Germany). The amount of luciferase expression was recorded in relative light units. Numbers were adjusted for control renilla luciferase expression and are expressed as the percentage of firefly luciferase expression in mice that did not receive injections containing siRNA.

Figure 7:
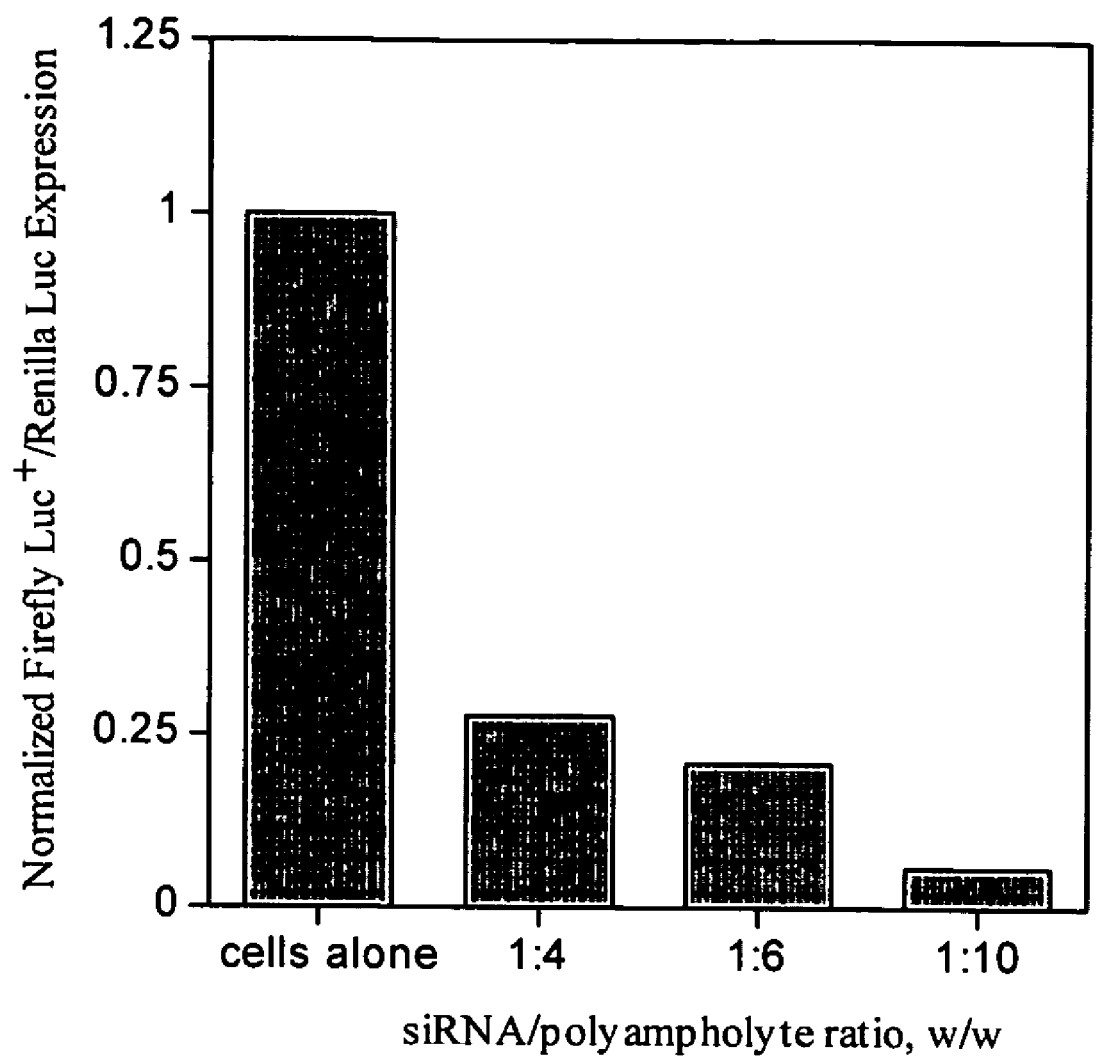
FIG. 7. Inhibition of firefly luciferase gene expression in mouse lungs achieved after IV administration of 50 μg siRNA (GL3) complexed with various amounts of brPEI-pAsp polyampholyte.

Conclusions: Complexes containing siRNA/brPEI were toxic to the animals and provided no inhibition of firefly luciferase activity (4 of 5 animal killed). SiRNA/brPEI complexes recharged with pAsp polymer were less toxic that siRNA/brPEI complexes, but did not result in siRNA mediated inhibition of luciferase activity (10–20% inhibition of luciferase expression). However, when siRNA-containing complexes were made using brPEI-pAsp polyampholytes, PEI toxicity was reduced and siRNA was functionally delivered to lung cells. Polyampholyte-mediated delivery of siRNA resulted in the gene-specific inhibition of firefly luciferase expression by 60% (FIG. 7).

Example 10

Delivery of siRNA to Cells in vitro Using Polyampholytes

Figure 8:
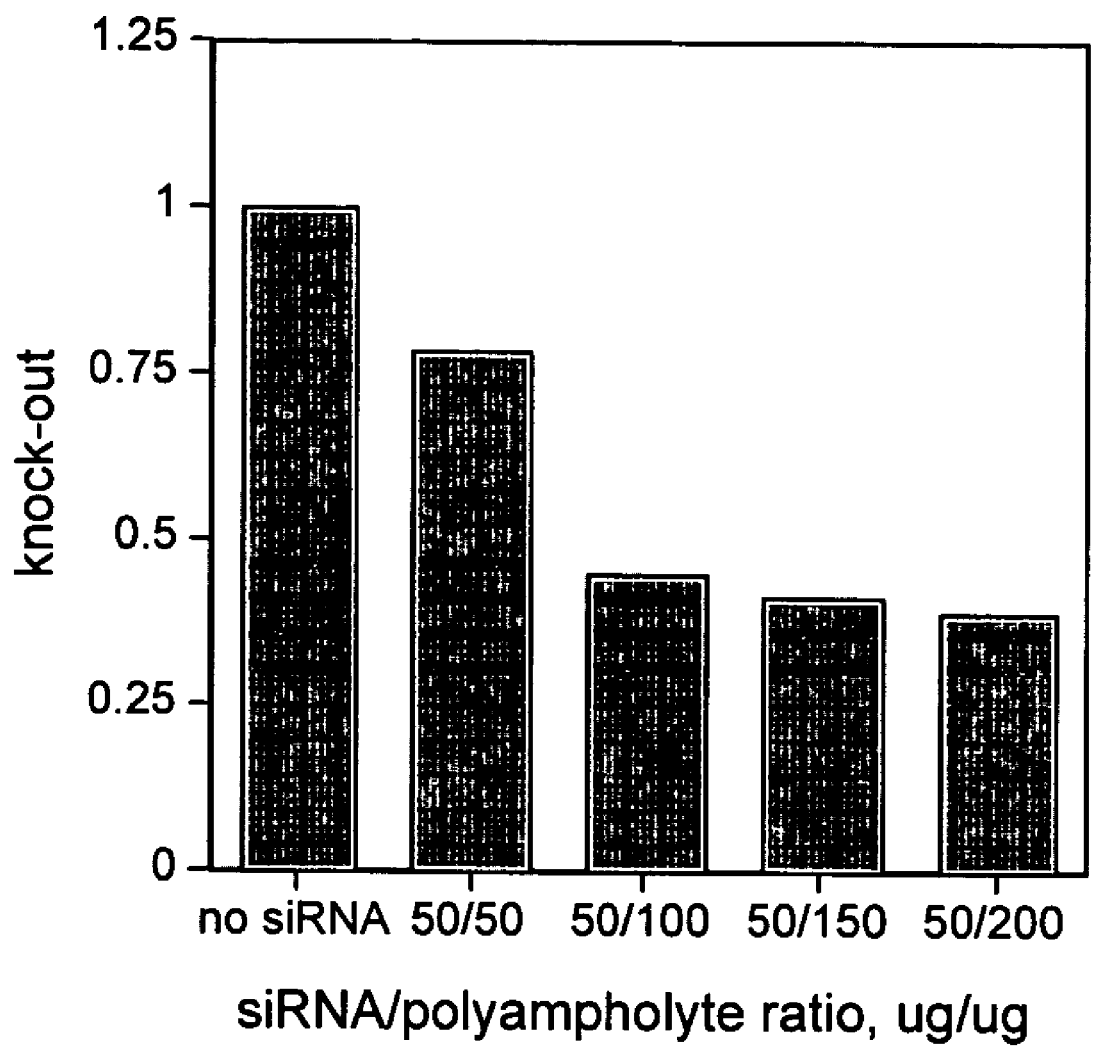
FIG. 8. Inhibition of firefly luciferase gene expression in COS7 after delivery of siRNA complexed with various amounts of brPEI-pAsp polyampholyte.

The polyampholyte brPEI-pAsp (2:1 w/w) was synthesized as described below. COS7 cells were initially transfected with two distinct luciferase genes encoding either firefly and renilla luciferase genes (pMIR116 and pMIR122, respectively) using TransIT LT1 according to the manufacturer's recommendations. Two hours after plasmid transfection, siRNA/polyampholyte complexes were added to cells. SiRNA/brPEI-pAsp complexes were prepared in 10 mM HEPES, 150 mM NaCl, pH 7.5 (HBS) immediately prior to transfections. The transfections were done in Opti-MEM supplemented with 10% fetal bovine serum. The concentration of siRNA was 40 nM. Luciferase activity was measured 24 h post-transfection. SiRNA delivery was measured by the ratio of firefly to renilla luciferase activity in the presence or absence of firefly specific siRNA. The data are shown in FIG. 8 and show that brPEI-pAsp polyampholyte complexes are effective in delivering siRNA to cells in vitro.

Example 11

Synthesis of Polyampholytes

A. Branched PEI (brPEI)-polyGlutamic acid (pGlu) and brPEI-polyAspartic acid (pAsp) pGlu (2.28 mg in 172 µl of water, pH 5.5) or pAsp (2 mg in 172 µL of water) were activated in the presence of 100 µg of EDC and N-hydroxysulfosuccinimide (Sulfo-NHS) each for 10-min at RT. BrPEI (4 mg) and 2.5 M Na Cl (0.5 ml) solutions were added to the activated polyanion. The reaction mixture was allowed to incubate for 5 h at RT. Resulting brPEI-based polyampholytes were dialyzed against water and freeze-dried.

B. Linear PEI (lPEI)-poly(Methacrylic acid) pMAA and lPEI-pGlu The following polyions were used for the reaction: lPEI (Mw=25 kDa, Polysciences), pMAA (MW=9.5 kDa, Aldrich), pGlu (MW=49 kDa, Sigma). For analytical purposes polyanions covalently labeled with rhodamine-ethylenediamine (Molecular Probes) were used for these reactions (degree of carboxy group modification<2%). pMAA (1 mg in 100 µL water) was activated in the presence of water-soluble carbodiimide (EDC, 100 µg) and Sulfo-NHS (100 µg) for 10 min at pH 5.5. Activated pMAA was added to the solution of lPEI (2 mg in 200 µL of 25 mM HEPES, pH 8.0) and incubated for 1 h at RT. pGlu was used at the same molar ratio.

After reaction completion, an equal volume of 3 M NaCl solution was added to a part of the reaction mixture. This part (0.5 ml) was passed through a Sepharose 4B-CL column (1×25 cm) equilibrated in 1.5 M NaCl and 1 ml fractions were collected. Rhodamine fluorescence was measured in each fraction. lPEI was measured using fluorescamine reaction. The amount of polyampholyte in the lPEI-pGlu reaction mixture was about 50%.

C. Melittin-pGlu (Partially Esterified with Di-(2-methyl-4-hydroxymethyl-1,3-dioxolane)-1,4-benzene). To a solution of the aldehyde-poly-glutamic acid compound (1.0 mg, 7.7 µmol) in water (200 µL) was added melittin (4.0 mg, 1.4 µmol) and the reaction mixture was stirred at RT for 12 h. The reaction mixture was then divided into two equal portions. One sample (100 µL) was dialyzed against 1% ethanol in water (2×1 L, 12,000–14,000 MWCO) and tested utilizing a theoretical yield of 1.7 mg. To the second portion (100 µL) was added sodium cyanoborohydride (1.0 mg, 16 µmol, Aldrich Chemical Company). The solution was stirred at RT for 1 h and then dialyzed against water (2×1 L, 12,000–14,000 MWCO).

D. CDM-DW297-DW301 pH-labile polyampholyte formed in the presence of DNA. Polycation DW297, was modified into a pH-labile polyanion by reaction with a 4 weight excess of CDM aldehyde in the presence of 25-fold weight equivalents HEPES base. DNA (10 µg/mL) in 5 mM HEPES pH 7.5 was condensed by the addition of polycation DW301(10 µg/mL). To the polycation-DNA particle was added the aldehyde-containing, pH-labile polyanion derived from DW297 (30 µg/mL). Particles formulated in this manner are 100–130 nm in size and are stable in 150 mM NaCl. The stability of particle size indicates that a covalent bond between the polycation and the polyanion of the complex has formed via an imine bond. In other words, the aldehyde of the polyanion has formed a bond with polycation, which results in the formation of a polyampholyte.

E. DM-KL$_3$-PLL, 2-propionic-3-methylmaleamic (CDM)-KL$_3$-PLL, and succinylated KL$_3$-PLL. See example 2D.

F. Poly-L-Glutamic acid (octamer)-Glutaric Dialdehyde Copolymer (MC151): H$_2$N-EEEEEEEE-NHCH$_2$CH$_2$NH$_2$ (SEQ ID 3; 5.5 mg, 0.0057 mmol, Gnostic) was taken up in 0.4 mL H$_2$O. Glutaric dialdehyde (0.52 µL, 0.0057 mmol, Aldrich Chemical Company) was added and the mixture was stirred at RT. After 10 min the solution was heated to 70° C. After 15 h, the solution was cooled to RT and dialyzed against H$_2$O(2×2 L, 3500 MWCO). Lyophilization afforded 4.3 mg (73%) poly-glutamic acid (octamer)-glutaric dialdehyde copolymer.

G. poly N-terminal acryloyl 6-aminohexanoyl-KLLKLLLKLWLKLLKLLLKLL-CO$_2$ (pAcKL$_3$; SEQ ID 4): A solution of AcKL$_3$ (20 mg, 7.7 µmol) in 0.5 mL of 6M guanidinium hydrochloride, 2 mM EDTA, and 0.5 M Tris pH 8.3 was degassed by placing under a 2 torr vacuum for 5 minutes. Polymerization of the acrylamide was initiated by the addition of ammonium persulfate (35 µg, 0.02 eq.) and N,N,N,N-tetramethylethylenediamine (1 µL). The polymerization was allowed to proceed overnight. The solution was then placed into dialysis tubing (12,000 molecular weight cutoff) and dialyzed against 3×2 L over 48 h. The amount of polymerized peptide (6 mg, 30% yield) was determined by measuring the absorbance of the tryptophan residue at 280 nm, using an extinction coefficient of 5690 cm$^{-1}$M$^{-1}$.

H. pH-labile polyampholytes using CDM-thioester and cysteine-modified polycations: A pH-labile polyanion is generated by the reaction of a polyamine with 2 equivalents (relative to amines) of CDM thioester. A cysteine-modified polycation is deprotected by reduction of disulfide with dithiothreitol. The thioester-containing, pH-labile polyanion is added to the cysteine-modified polycation. The thioester groups and cysteine groups react to produce a pH-labile polyampholyte. Polycations that can modified with cysteine and used as pH-labile polyanion may be selected from the group comprising: PLL, polyallylamine, polyvinylamine, polyethyleneimine, and histone H1.

I. A method for synthesizing such a polyampholyte is to react amine-containing compounds with poly (methylvinylether maleic anhydride) pMVMA. The anhydride of pMVMA reacts with amines to form an amide and an acid. Two different amine and imidazole containing compounds were used: histidine, which also attaches a carboxylic acid group, and histamine which just attaches an imidazole group. The histidine containing polymer (MC#486) and the histamine containing polymer (MC#510) are alternating copolyampholytes.

MC510: To a solution of poly(methyl vinyl ether-alt-maleic anhydride) (purchased from Aldrich Chemical) 50 mg in 10 mL of anhydrous tetrahydrofuran was added 100 mg of histamine. The solution was stirred for 1 h followed by the addition of 10 mL water. The solution was stirred for another hour and then placed into a 12,000 MW cutoff dialysis tubing and dialyzed against 7×4 L water over a one week period. The solution was then removed from the dialysis tubing and then concentrated to 1 mL volume by lyophilization.

MC486: To a solution of histidine (150 mg) and potassium carbonate (150 mg) in 10 mL water was added 50 mg of poly(methyl vinyl ether-alt-maleic anhydride) (purchased from Aldrich Chemical). The solution was stirred for 1 h and then placed into a 12,000 MW cutoff dialysis tubing and dialyzed against 7×4 L water over a one week period. The solution was then removed from the dialysis tubing and then concentrated to 1 mL volume by lyophilization.

To determine the effect of pH on these MC510 and MC486, we measured the amount of polymer needed to condense fluorescein-labeled polylysine at pH 7.5 and pH 6.0. As fluorescein-labeled polylysine is condensed by addition of a negatively charged polyelectrolyte, the fluorescein fluorophores are brought closer together, causing fluorescence to be quenched. This quenching enables one to measure the extent of condensation and thus the charge density of the polyelectrolyte. The histamine containing polymer, MC#510, required significantly more material to condense the polylysine at pH 6.0 than at pH 7.5. Approximately five-fold more polymer was required. The histidine-containing polymer, MC#486, also need more material at pH 6.0, approximately two-fold more. These data suggest that we have made polyanions which are pH-sensitive in a pH range that is important for endosomal release.

J. Polyallylamine-graft imidazoleacetic acid polycation (DW163): Polyallylamine (15,000 MW) is dissolved to 50 mg/mL in 100 mM MES (pH 6.5) buffer in a 15-ml polypropylene tube. To this solution is added 1.1 molar equivalent (relative to amine content of polyallylamine) of 4-imidazoleacetic acid. N-(3-Dimethylaminopropyl)-N'-ethylcarbodiimide (EDC) (1.1 equivalent) and N-hydroxysuccinimide (1.1 equivalent) are dissolved in 2 ml of MES buffer and are added immediately to the polyallylamine solution. The reaction tube was sealed and allowed to react at RT for 24 h. The reaction mixture is then removed from tube and placed into dialysis tubing (3,500 MW cutoff), and dialyzed against 7×4 L water over a one week period. The polymer is then removed from the tubing and concentrated by lyophilization to 10 mg/mL.

K. MC750: To a solution of poly(methyl vinyl ether-alt-maleic anhydride) (purchased from Aldrich Chemical) 50 mg in 10 mL of anhydrous tetrahydrofuran was added 100 mg of 1-(3-aminopropyl)imidazole. The solution was stirred for 1 h followed by the addition of 10 mL water. The solution was stirred for another hour and then placed into a 12,000 MW cutoff dialysis tubing and dialyzed against 7×4 L water over a one week period. The solution was then removed from the dialysis tubing and then concentrated to 1 mL volume by lyophilization.

L. Acetal-containing polyampholyte DW179A and DW179B: To a solution of poly(methyl vinyl ether-alt-maleic anhydride) (purchased from Aldrich Chemical) 20 mg in 5 mL of anhydrous tetrahydrofuran was added 1.4 or 3.5 µL of aminoacetaldehyde dimethyl acetal (0.01 or 0.025 mol eq.) and this solution was stirred for 3 h followed by the addition of 80 mg of histamine. The solution was then stirred for 24 h followed by the addition of 10 mL water. The solution was stirred for another hour and then placed into a 12,000 MW cutoff dialysis tubing and dialyzed against 7×4 L water over a one week period. The solution was then removed from the dialysis tubing and then concentrated to 1 mL volume by lyophilization.

The polyampholyte containing 0.01 eq acetal was given the number DW#179A and the polyampholyte containing 0.025 eq acetal was given the number DW#179B. The acetal groups of DW#179 were removed to produce aldehyde groups by placing 1 mg of DW179 into 1 mL centrifuge tube, and adjusting the pH to 3.0 with 1M HCl and left at RT 12 h. After incubation at acidic pH, the DW#179 may be added to polyamine-condensed DNA to form a Schiff between the amine and the aldehyde thus forming a polyampholyte.

M. Poly(Acrylic acid-co-maleic acid) graft Histamine Polymer (MC758): A solution of Poly(Acrylic acid-co-maleic acid)(0.050 g, 0.026 mmol), histamine (0.029 g, 0.026 mmol) were dissolved in 5 mL of 100 mM 2-[N-morpholino] ethanesulfonic acid(MES) at pH 6.5. This solution was then added to 1,[3-(dimethylamino)propyl]-3-ethylcarboimide (EDC, 0.057 g, 0.029 mmol), followed by the addition of N-hydroxy-succinimide (NHS, 0.033 g, 0.029 mmol) in 0.5 mL of pH 6.5 100 mM MES. This solution was sealed tightly and stirred for 24 h at RT. This solution was then transferred to 12,000 to 14,000 molecular weight tubing and dialyzed against distilled water for 4 days, and freeze dried.

N. Poly(Acrylic acid-co-maleic acid) graft 1-(3-aminopropyl) imidazole Polymer (MC757): Poly(Acrylic acid-co-maleic acid) (0.050 g, 0.026 mmol), and 1-(3-amino-propyl) imidazole (0.0155 g, 0.013 mmol) were dissolved in 5 mL of 100 MES at pH 6.5. This solution was then added to 1,[3-(dimethylamino)propyl]-3-ethylcarboimide (EDC, 0.0312 g, 0.016 mmol), followed by the addition of N-hydroxysuccinimide (NHS, 0.012 g, 0.016 mmol) in 0.5 mL of pH 6.5 100 mM MES. This solution was sealed tightly and stirred for 24 h at RT. This solution was then transferred to 12,000 to 14,000 molecular weight tubing and dialyzed against distilled water for 4 days, and freeze dried.

Example 12

Synthesis of Compounds Utilized in the Formation of Polyampholytes

A. 2-propionic-3-methylmaleic anhydride (carboxydimethylmaleic anhydride or CDM): To a suspension of sodium hydride (0.58 g, 25 mmol) in 50 mL anhydrous tetrahydrofuran was added triethyl-2-phosphonopropionate (7.1 g, 30 mmol). After bubbling of hydrogen gas stopped, dimethyl-2-oxoglutarate (3.5 g, 20 mmol) in 10 mL anhydrous tetrahydrofuran was added and stirred for 30 minutes. Water, 10 mL, was then added and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether:hexane to yield 4 g (82% yield) of pure triester. The 2-propionic-3-methylmaleic anhydride then formed by dissolving of this triester into 50 mL of a 50/50 mixture of water and ethanol containing 4.5 g (5 equivalents) of potassium hydroxide. This solution was heated to reflux for 1 h. The ethanol was then removed by rotary evaporation and the solution was acidified to pH 2 with hydrochloric acid. This aqueous solution was then extracted with 200 mL ethyl acetate, which was isolated, dried with magnesium sulfate, and concentrated to a white solid. This solid was then recrystallized from dichloromethane and hexane to yield 2 g (80% yield) of 2-propionic-3-methylmaleic anhydride.

B. 2,3-dioleoyldiaminopropionic ethylenediamine amide: 2,3-diaminopropionic acid (1.4 g, 10 mmol) and dimethylaminopyridine (1.4 g 11 mmol) were dissolved in 50 mL of water. To this mixture was added over 5 minutes with rapid stirring oleoyl chloride (7.7 mL, 22 mmol) of in 20 mL of tetrahydrofuran. After all of the acid chloride had been added, the solution was allowed to stir for 30 minutes. The pH of the solution was 4 at the end of the reaction. The tetrahydrofuran was removed by rotary evaporation. The mixture was then partitioned between water and ethyl acetate. The ethyl acetate was isolated, dried with magnesium sulfate, and concentrated by rotary evaporation to yield a yellow oil. The 2,3-dioleoyl-diaminopropionic acid was isolated by silica gel chromatography, elution with ethyl ether to elute oleic acid, followed by 10% methanol 90% methylene chloride to elute diamide product, 1.2 g (19% yield). The diamide (1.1 g, 1.7 mmol) was then dissolved in 25 mL of methylene chloride. To this solution was added N-hydroxysuccinimide (0.3 g, 1.5 eq) and dicyclohexylcarbodiimide (0.54 g, 1.5 eq). This mixture was allowed to stir overnight. The solution was then filtered through a cellulose plug. To this solution was added ethylene diamine (1 g, 10 eq) and the reaction was allowed to proceed for 2 h. The solution was then concentrated by rotary evaporation. The resulting solid was purified by silica gel chromatography elution with 10% ammonia saturated methanol and 90% methylene chloride to yield the triamide product 2,3-di-oleoyldiaminopropionic ethylenediamine amide (0.1 g, 9% yield). The triamide product was given the number MC213.

C. Dioleylamideaspartic acid: N-(tert-butoxycarbonyl)-L-aspartic acid (0.5 g, 2.1 mmol) was dissolved in 50 mL of acetonitrile. To this solution was added N-hydroxy-succinimide (0.54 g, 2.2 eq) and was added dicyclohexylcarbodiimide (0.54 g, 1.5 eq). This solution was allowed to stir overnight. The solution was then filtered through a cellulose plug. This solution was then added over 6 h to a solution containing oleylamine (1.1 g, 2 eq) in 20 mL methylene chloride. After the addition was complete the solvents were removed by rotary evaporation. The resulting solid was partitioned between 100 mL ethyl acetate and 100 mL water. The ethyl acetate fraction was then isolated, dried by sodium sulfate, and concentrated to yield a white solid. The solid was dissolved in 10 mL of triflouroacetic acid, 0.25 mL water, and 0.25 mL triisopropylsilane. After two h, the triflouroacetic acid was removed by rotary evaporation. The product was then isolated by silica gel chromatography using ethyl ether followed by 2% methanol 98% methylene chloride to yield 0.1 g (10% yield) of pure dioleylamideaspartic acid, which was given the number MC303.

D. Dimethylmaleamic-peptides: Solid melittin or pardaxin or other peptide (100 µg) was dissolved in 100 µL of anhydrous dimethylformamide containing 1 mg of 2,3-dimethyl-maleic anhydride and 6 µL of diisopropylethylamine. Similar procedures were used for derivatives of dimethylmaleic anhydride such as 2-propionic-3-methylmaleic anhydride (CDM) and CDM-thioester.

E. Polyethyleneglycol methyl ether 2-propionic-3-methylmaleate (CDM-PEG): To a solution of 2-propionic-3-methylmaleic anhydride ( 30 mg, 0.16 mmol) in 5 mL methylene chloride was added oxalyl chloride (200 mg, 10 eq) and dimethylformamide (1 µL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added polyethyleneglycol monomethyl ether, molecular weight average of 5,000 (815 mg, 1 eq) and pyridine (20 µL, 1.5 eq) in 10 mL of methylene chloride. The solution was then stirred overnight. The solvent was then removed and the resulting solid was dissolved into 8.15 mL of water.

F. Polyvinyl(2-phenyl-4-hydroxymethyl-1,3-dioxolane) from the reaction of Polyvinylphenyl Ketone and Glycerol: Polyvinyl phenyl ketone (500 mg, 3.78 mmol, Aldrich Chemical Company) was taken up in 20 mL dichloromethane. Glycerol (304 µL, 4.16 mmol, Acros Chemical Company) was added followed by p-toluenesulfonic acid monohydrate (108 mg, 0.57 mmol, Aldrich Chemical Company). Dioxane (10 mL) was added and the solution was stirred at RT overnight. After 16 h, TLC indicated the presence of ketone. The solution was concentrated under reduced pressure, and the residue dissolved in dimethylformamide (7 mL). The solution was heated to 60° C. for 16 h. After 16 h, TLC indicated the ketone had been consumed. Dialysis against $H_2O$ (1×3 L, 3500 MWCO), followed by lyophilization resulted in 606 mg (78%) of the ketal. Ketone was not observed in the sample by TLC analysis, however, upon treatment with acid, the ketone was again detected.

G. Peptide synthesis: Peptide syntheses were performed using standard solid phase peptide techniques using FMOC chemistry.

H. Coupling $KL_3$ to poly(allylamine): To a solution of poly(allylamine) (2mg) in water (0.2 mL) was added $KL_3$ (0.2 mg, 2.5 eq) and 1-(3-dimethylaminopropyl)-3-ethylcarbodiimide hydrochloride (1 mg, 150 eq). The reaction was allowed to react for 16 h and then the mixture was placed into dialysis tubing and dialyzed against 3×1 L for 48 h. The solution was then concentrated by lyophilization to 0.2 mL.

I. Aldehyde adduct of 2-propionic-3-methylmaleic anhydride (CDM-aldehyde): To a solution of 2-propionic-3-methylmaleic anhydride (CDM) 50 mg in 5 mL methylene chloride was added 1 mL oxalyl chloride. The solution was stirred overnight at RT. The excess oxalyl chloride and methylene chloride was removed by rotary evaporation to yield a clear oil. The oil was then dissolved in methylene chloride (5 mL) and 85 mg of 2,2-dimethoxyethylamine was added. The solution was added to proceed for 1 h. The solvent was removed by rotary evaporation to yield a yellow oil which was placed under high vacuum (1 torr) for 24 h. The resulting oil was dissolved in 5 mL water and chromatographed by reverse-phase HPLC eluting with acetonitrile containing 0.1% trifluoroacetic acid to produce the dimethyl acetal (20 mg). To remove the acetal, it was dissolved in 1 mL acetonitrile and 0.1 mL concentrated hydrochloric acid. The aldehyde was isolated by reverse-phase HPLC eluting with acetonitrile containing 0.1% trifluoroacetic acid to produce 10 mg of aldehyde adduct of 2-propionic-3-methylmaleic anhydride (CDM-aldehyde).

J. Mercaptoacetic acid thioester of 2-propionic-3-methylmaleic anhydride (CDM thioester): To a solution of 2-propionic-3-methylmaleic anhydride (CDM) 50 mg in 5 mL methylene chloride was added 1 mL oxalyl chloride. The solution was stirred overnight at RT. The excess oxalyl chloride and methylene chloride was removed by rotary evaporation to yield a clear oil. The oil was then dissolved in methylene chloride (5 mL) and 25 mg of mercaptoacetic acid was added, followed by the addition of 70 mg of diisopropylethylamine. After 1 h, the solvent was removed by rotary evaporation and excess mercaptoacetic acid and diisopropylethylamine were removed by placing the sample under high vacuum (1 torr) for 24 h. The resulting oil was dissolved in 5 mL water and chromatographed by reverse-phase HPLC eluting with acetonitrile containing 0.1% trifluoroacetic acid to produce the thioester.

Example 13

Synthesis of acid Labile Monomers

A. Di-(2-methyl4-hydroxymethyl-1,3-dioxolane)-1,4-benzene (MC216). To a solution of diacetylbenzene (2.00 g, 12.3 mmol, Aldrich Chemical Company) in toluene (30.0 mL), was added glycerol (5.50 g, 59.7 mmol, Acros Chemical Company) followed by p-toluenesulfonic acid monohydrate (782 mg, 4.11 mmol, Aldrich Chemical Company). The reaction mixture was heated at reflux for 5 h with the removal of water by azeotropic distillation in a Dean-Stark trap. The reaction mixture was concentrated under reduced pressure, and the residue was taken up in Ethyl Acetate. The solution was washed 1× with 10% $NaHCO_3$, 3× with $H_2O$, 1× with brine, and dried ($MgSO_4$). Following removal of solvent (aspirator), the residue was purified by flash chromatography on silica gel (20×150 mm, $CH_2Cl_2$ eluent) to afford 593 mg (16% yield) of di-(2-methyl-4-hydroxymethyl-1,3-dioxolane)-1,4-benzene. Molecular ion calculated for $C_{16}H_{22}O_6$, 310. found m+1/z 311.2; 300 MHz NMR ($CDCl_3$, ppm) δ 7.55–7.35 (4H, m) 4.45–3.55 (10H, m) 1.65 (6 H, brs).

B. Di-(2-methyl-4-hydroxymethyl(succinic semialdehyde ester)-1,3-dioxolane)-1,4-benzene (MC 211): To a solution of succinic semialdehyde (150 mg, 1.46 mmol, Aldrich Chemical Company) and di-(2-methyl-4-hydroxymethyl-1,3-dioxolane)-1,4-benzene (150 mg, 480 μmol) in $CH_2Cl_2$ (4 mL) was added dicyclohexylcarbodiimide (340 mg, 1.65 mmol, Aldrich Chemical Company) followed by a catalytic amount of 4-dimethyl-aminopyridine. The solution was stirred for 30 min and filtered. Following removal of solvent (aspirator), the residue was purified by flash chromatography on silica gel (20×150 mm, $CH_2Cl_2$ eluent) to afford 50 mg (22%) of di-(2-methyl-4-hydroxy-methyl(succinic semi- aldehyde ester)-1,3-dioxolane)-1,4-benzene. Molecular ion calculated for $C_{24}H_{30}O_{10}$, 478.0. found m+1/z 479.4.

C. Di-(2-methyl-4-hydroxymethyl(glyoxilic acid ester)-1,3-dioxolane)-1,4-benzene (MC225): To a solution of glyoxylic acid monohydrate (371 mg, 403 μmol, Aldrich Chemical Company) and di-(2-methyl-4-hydroxymethyl-1,3-dioxolane)-1,4-benzene (500 mg, 161 μmol) in dimethylformamide (8 mL) was added dicyclohexylcarbodiimide (863 mg, 419 μmol, Aldrich Chemical Company). The solution was stirred for 30 min and filtered. Following removal of solvent (aspirator), the residue was purified by flash chromatography on silica gel (20×150 mm, ethylacetate/Hexanes (1:2.3 eluent) to afford 58 mg (10%) of di-(2-methyl-4-hydroxymethyl(glyoxylic acid ester)-1,3-dioxolane)-1,4-benzene.

D. Synthesis of Di-(2-methyl-4-aminomethyl-1,3-dioxolane)-1,4-benzene (MC372): To a solution of 1,4-diacetylbenzene (235 mg, 1.45 mmol, Aldrich Chemical Company) in toluene (15.0 mL) was added 3-amino-1,2-propanediol protected as the FMOC carbamide (1.0 g, 3.2 mmol), followed by a catalytic amount of p-toluenesulfonic acid monohydrate (Aldrich Chemical Company). The reaction mixture was heated at reflux for 16 h with the removal of water by azeotropic distillation in a Dean-Stark trap. The reaction mixture was cooled to RT, partitioned in toluene/ $H_2O$, washed 1×10% $NaHCO_3$, 3× $H_2O$, 1×brine, and dried ($MgSO_4$). The extract was concentrated under reduced pressure and crystallized (methanol/$H_2O$). The protected amine ketal was identified in the supernatant, which was concentrated to afford 156 mg product. The free amine was generated by treating the ketal with piperidine in dichloromethane for 1 h.

E. Di-(2-methyl-4-hydroxymethyl(glycine ester)-1,3-dioxolane)-1,4-benzene (MC373): To a solution of FMOC-Glycine (690 mg, 2.3 mmol, NovaBiochem) in dichloromethane (4.0 mL) was added dicyclohexylcarbodiimide (540 mg, 2.6 mmol, Aldrich Chemical Company). After 5 min, di-(2-methyl-4-hydroxymethyl-1,3-dioxolane)-1,4-benzene (240 mg, 770 μmol) was added followed by a catalytic amount of 4-dimethylamino-pyridine. After 20 min, the reaction mixture was filtered and concentrated (aspirator) to afford 670 mg oil. The residue was taken in tetrahydrofuran (4.0 mL) and piperidine (144 mg, 1.7 mmol) was added. The reaction was stirred at RT for 1 h and added to cold diethyl ether. The resulting solid was washed 3× diethyl ether to afford di-(2-methy4-hydroxymethyl(glycine ester)-1,3-dioxolane)-1,4,benzene. Molecular ion calculated for $C_{20}H_{28}N_2O_8$, 424. found m+1/z 425.2.

Example 14

Synthesis of Polyanions

A. 2,3-dimethylmaleamic poly-L-lysine: Poly-L-lysine (10 mg 34,000 MW Sigma Chemical) was dissolved in 1 mL of aqueous potassium carbonate (100 mM). To this solution was added 2,3-dimethylmaleic anhydride (100 mg, 1 mmol) and the solution was allowed to react for 2 h. The solution was then dissolved in 5 mL of aqueous potassium carbonate (100 mM) and dialyzed against 3×2 L water that was at pH8 with addition of potassium carbonate. The solution was then concentrated by lyophilization to 10 mg/mL of 2,3-dimethylmaleamic poly-L-lysine.

B. Melittin-PAA, $KL_3$-PAA, Melittin-PLL, and $KL_3$-PLL with dimethylmaleic anhydride (DM) and 2-propionic-3-methylmaleic anhydride (CDM), general procedure: Peptide-polycation conjugates (10 mg/mL) in water were reacted with a ten-fold weight excess of dimethylmaleic anhydride and a ten-fold weight excess of potassium carbonate. Analysis of the amine content after 30 by addition of peptide solution to 0.4 mM TNBS and 100 mM borax revealed no detectable amounts of amine.

C. Polyvinyl(2-methyl-4-hydroxymethyl(succinic anhydride ester)-1,3-dioxolane: To a solution of polyvinyl(2-methyl-4-hydroxymethyl-1,3-dioxolane) (220 mg, 1.07 mmol) in dichloromethane (5 mL) was added succinic anhydride (161 mg, 1.6 mmol, Sigma Chemical Company), followed by diisopropylethyl amine (0.37 mL, 2.1 mmol, Aldrich Chemical Company) and the solution was heated at reflux. After 16 h, the solution was concentrated, dialyzed against $H_2O$ (1×3 L, 3500 MWCO), and lyophilized to afford 250 mg (75%) of the ketal acid polyvinyl(2-methyl-4-hydroxymethyl(succinic anhydride ester)-1,3-dioxolane.

D. Ketal from Polyvinyl Alcohol and 4-Acetylbutyric Acid: Polyvinylalcohol (200 mg, 4.54 mmol, 30,000–60,000 MW, Aldrich Chemical Company) was taken up in dioxane (10 mL). 4-acetylbutyric acid (271 µL, 2.27 mmol, Aldrich Chemical Company) was added followed by p-toluenesulfonic acid monohydrate (86 mg, 0.45 mmol, Aldrich Chemical Company). After 16 h, TLC indicated the presence of ketone. The solution was concentrated under reduced pressure, and the residue dissolved in dimethylformamide (7 mL). The solution was heated to 60° C. for 16 h. After 16 h, TLC indicated the loss of ketone in the reaction mixture. Dialysis against $H_2O$ (1×4 L, 3500 MWCO), followed by lyophilization resulted in 145 mg (32%) of the ketal. Ketone was not observed in the sample by TLC analysis, however, upon treatment with acid, the ketone was again detected.

E. Partial Esterification of Poly-Glutamic Acid with Di-(2-methyl4-hydroxymethyl-1,3-dioxolane)-1,4-benzene (MC 196): To a solution of poly-L-glutamic acid (103 mg, 792 µmol, 32,000 MW, Sigma Chemical Company) in sodium phosphate buffer (30 mM) was added 1-(3-dimethylaminopropyl)-3-ethylcarbodiimide hydrochloride (129 mg, 673 µmol, Aldrich Chemical Company), followed by di-(2-methyl-4-hydroxymethyl-1,3-dioxolane)-1,4-benzene (25.0 mg, 80.5 µmol), and a catalytic amount of 4-dimethylaminopyridine. After 12 h, the reaction mixture was dialyzed against water (2×1 L, 12,000–14,000 MWCO) and lyophilized to afford 32 mg of poly-glutamic acid partially esterified with di-(2-methyl-4-hydroxymethyl-1,3-dioxolane)-1,4-benzene.

F. Aldehyde Derivatization of the Poly-Glutamic Acid Partially Esterified with Di-(2-methyl-4-hydroxymethyl-1, 3-dioxolane)-1,4-benzene: To a solution of succinic semialdehyde (2.4 mg, 23 µmol, Aldrich Chemical Company) in water (100 µL) was added 1-(3-dimethyl-aminopropyl)-3-ethylcarbodiimide hydrochloride (4.7 mg, 2.4 µmol, Aldrich Chemical Company) followed by N-hydroxysuccinimide (2.8 mg, 24 µmol, Aldrich Chemical Company). The reaction was stirred at RT for 20 min. Formation of the N-hydroxysuccinic ester of succinic semialdehyde was confirmed by mass spectrometry.

Poly-glutamic acid partially esterified with di-(2-methyl-4-hydroxymethyl-1,3-dioxolane)-1,4-benzene (15.0 mg, 115 µmol) was taken up in water (100 µL) and added to the N-hydroxysuccinic ester of succinic semialdehyde, followed by a crystal of 4-dimethylaminopyridine. The reaction mixture was stirred overnight at RT. After 12 h the reaction mixture was dialyzed against water (2×1 L, 12,000–14,000 MWCO) and lyophilized to afford 3.0 mg. After dialysis the product tested positive for aldehyde content with 2,4-di-nitrophenylhydrazine.

G. polypropylacrylic acid: To a solution of diethylpropylmalonate (2 g, 10 mmol) in 50 mL ethanol was added potassium hydroxide (0.55 g, 1 eq) and the mixture was stirred at RT for 16 h. The ethanol was then removed by rotary evaporation. The reaction mixture was partitioned between 50 mL ethyl acetate and 50 mL of water. The aqueous solution was isolated, and acidified with hydrochloric acid. The solution was again partitioned between ethyl acetate and water. The ethyl acetate layer was isolated, dried with sodium sulfate, and concentrated to yield a clear oil. To this oil was added 20 mL of pyridine, paraformaldehyde (0.3 g, 10 mmol), and 1 mL piperidine. The mixture was refluxed at 130° C. until the evolution of gas was observed, ca. 2 h. The ester product was then dissolved into 100 mL ethyl ether, which was washed with 100 mL 1M hydrochloric acid, 100 mL water, and 100 mL saturated sodium bicarbonate. The ether layer was isolated, dried with magnesium sulfate, and concentrated by rotary evaporation to yield a yellow oil. The ester was then hydrolyzed by dissolving in 50 mL ethanol with addition of potassium hydroxide (0.55 g, 10 mmol). After 16 h, the reaction mixture was acidified by the addition of hydrochloric acid. The propylacrylic acid was purified by vacuum distillation (0.9 g, 80% yield), boiling point of product is 60° C. at 1 torr. The propylacrylic acid was polymerized by addition of 1 mole percent of azobisisobutyo-nitrile and heating to 60° C. for 16 h. The polypropylacrylic acid was isolated by precipitation with ethyl ether.

H. 5,5'-Dithiobis(2-nitrobenzoic acid)-Poly-Glutamic acid (8mer) Copolymer: $H_2N$-EEEEEEEE-$NHCH_2CH_2NH_2$ (SEQ ID 3; 5.0 mg, 0.0052 mmol, Gnostic) was taken up in 0.1 mL HEPES (250 mM, pH 7.5). 5,5'-dithiobis[succinimidyl(2-nitrobenzoate)] (3.1 mg, 0.0052) was added with 0.2 mL DMSO and the mixture was stirred overnight at RT. After 16 h the solution was heated to 70° C. for 10 min, cooled to RT and diluted to 1.10 mL with DMSO.

Example 15

Synthesis of Polycations

A. L-cystine-1,4-bis(3-aminopropyl)piperazine copolymer: To a solution of N,N'-Bis(t-BOC)-L-cystine (85 mg, 0.15 mmol) in ethyl acetate (20 mL) was added N,N'-dicyclohexylcarbodiimide (108 mg, 0.5 mmol) and N-hydroxysuccinimide (60 mg, 0.5 mmol). After 2 h, the solution was filtered through a cotton plug and 1,4-bis(3-aminopropyl)piperazine (54 µL, 0.25 mmol) was added. The reaction was allowed to stir at RT for 16 h. The ethyl acetate was then removed by rotary evaporation and the resulting solid was dissolved in trifluoroacetic acid (9.5 mL), water (0.5 mL) and triisopropylsilane (0.5 mL). After 2 h, the trifluoroacetic acid was removed by rotary evaporation and the aqueous solution was dialyzed in a 15,000 MW cutoff tubing against water (2×21) for 24 h. The solution was then removed from dialysis tubing, filtered through 5 µM nylon syringe filter and then dried by lyophilization to yield 30 mg of polymer.

B. Adducts between peptides and polyamines: To a solution of poly-L-lysine (10 mg, 0.2 µmol) or polyallylamine (10 mg, 0.2 µmol) and peptides, such as $KL_3$ or melittin (2 µmol), was added 1-(3-dimethylaminopropyl)-3-ethylcarbodiimide hydrochloride (20 µmol). For the peptide $KL_3$, the reaction was performed in 2 mL water. For the peptide melittin, the reaction was performed in a solution of 1 mL water and 1 mL triflouroethanol. The reaction was allowed to proceed overnight before placement into a 12,000 molecular weight cutoff dialysis bag and dialysis against 4×2 liters over 48 h. The amount of coupled peptide was determined by the absorbance at 280 nm of a peptide tryptophan residue, using an extinction coefficient of 5690 cm$^{-1}$M$^{-1}$. The conjugate of melittin and poly-L-lysine was determined to have 4 molecules of melittin per molecule of poly-L-lysine and is referred to as Mel-PLL. The conjugate of KL$_3$ and poly-L-lysine was determined to have 10 molecules of KL$_3$ per molecule of poly-L-lysine and is referred to as KL$_3$-PLL. The conjugate melittin and polyallylamine was determined to have 4 molecules of melittin per molecule of polyallylamine and is referred to as Mel-PAA. The conjugate of KL$_3$ and polyallylamine was determined to have 10 molecules of KL$_3$ per molecule of polyallylamine and is referred to as KL$_3$-PAA.

C. Di-(2-methyl-4-hydroxymethyl(glyoxilic acid ester)-1, 3-dioxolane)-1,4-benzene: 1,4-Bis(3-aminopropyl)piperazine Copolymer (1:1) (MC228): To a solution of di-(2-methyl4-hydroxymethyl(glyoxylic acid ester)-1,3-dioxolane) 1,4-benzene (100 mg, 0.273 mmol) in dimethylformamide was added 1,4-bis(3-aminopropyl)-piperazine (23 μL, 0.273 mmol, Aldrich Chemical Company) and the solution was heated to 80° C. After 16 h the solution was cooled to RT and precipitated with diethyl ether. The solution was decanted and the residue washed with diethyl ether (2×) and dried under vacuum to afford di-(2-methyl-4-hydroxymethyl(glyoxylic acid ester)-1,3-dioxolane) 1,4-benzene: 1,4-bis(3-aminopropyl)-piperazine copolymer (1:1). By similar methods the following polymers were constructed:

1. Di-(2-methyl-4-hydroxymethyl(succinic semialdehyde ester)-1,3-dioxolane)-1,4-benzene: 1,4-Bis(3-aminopropyl)piperazine Copolymer (1:1) (MC208).
2. Di-(2-methyl4-hydroxymethyl(succinic semialdehyde ester)-1,3-dioxolane)-1,4-benzene: 1,4-Bis(3-aminopropyl)piperazine Copolymer (1:1) Reduced with NaCNBH$_3$ (MC301).
3. Di-(2-methyl-4-hydroxymethyl(succinic semialdehyde ester)-1,3-dioxolane)-1,4-benzene: 1,3-Diaminopropane Copolymer (1:1) (MC300).
4. Di-(2-methyl4-hydroxymethyl(succinic semialdehyde ester)-1,3-dioxolane)-1,4-benzene: 3,3'-Diamino-N-methyldipropylamine Copolymer (1:1) (MC218).
5. Di-(2-methyl-4-hydroxymethyl(succinic semialdehyde ester)-1,3-dioxolane)-1,4-benzene: Tetraethylenepentamine Copolymer (1:1) (MC217).
6. Di-(2-methyl-4-hydroxymethyl(glyoxilic acid ester)-1, 3-dioxolane)-1,4-benzene: 1,3-Diaminopropane Copolymer (1:1) (MC226).
7. Di-(2-methyl-4-hydroxymethyl(glyoxilic acid ester)-1, 3-dioxolane)-1,4-benzene: 3,3'-Diamino-N-methyldipropylamine Copolymer (1:1) (MC227).

D. 1,4-Bis(3-aminopropyl)piperazine-Glutaric Dialdehyde Copolymer (MC140): 1,4-Bis(3-aminopropyl)piperazine (206 μL, 0.998 mmol, Aldrich Chemical Company) was taken up in 5.0 mL H$_2$O. Glutaric dialdehyde (206 μL, 0.998 mmol, Aldrich Chemical Company) was added and the solution was stirred at RT. After 30 min, an additional portion of H$_2$O was added (20 mL), and the mixture neutralized with 6 N HCl to pH 7, resulting in a red solution. Dialysis against H$_2$O (3×3 L, 12,000–14,000 MWCO) and lyophilization afforded 38 mg (14%) of the copolymer. By similar methods the following polymers were constructed:

1. Diacetylbenzene—1,3-Diaminopropane Copolymer(1:1) (MC321)
2. Diacetylbenzene—Diamino-N-methyldipropylamine Copolymer (1:1) (MC322).
3. Diacetylbenzene—1,4-Bis(3-aminopropyl)piperazine Copolymer (1:1) (MC229)
4. Diacetylbenzene—Tetraethylenepentamine Copolymer (1:1) (MC323).
5. Glutaric Dialdehyde—1,3-Diaminopropane Copolymer (1:1) (MC324)
6. Glutaric Dialdehyde—Diamino-N-methyldipropylamine Copolymer (1:1) (MC325).
7. Glutaric Dialdehyde—Tetraethylenepentamine Copolymer (1:1) (MC326).
8. 1,4-Cyclohexanone—1,3-Diaminopropane Copolymer (1:1) (MC330)
9. 1,4-Cyclohexanone—Diamino-N-methyldipropylamine Copolymer (1:1) (MC331).
10. 1,4-Cyclohexanone—1,4-Bis(3-aminopropyl)piperazine Copolymer (1:1) (MC312)
11. 1,4-Cyclohexanone—Tetraethylenepentamine Copolymer (1:1) (MC332).
12. 2,4-Pentanone—1,4-Bis(3-aminopropyl)piperazine Copolymer (1:1) (MC340)
13. 2,4-Pentanone—Tetraethylenepentamine Copolymer (1:1) (MC347).
14. 1,5-Hexafluoro-2,4-Pentanone—1,4-Bis(3-aminopropyl)piperazine Copolymer (1:1) (MC339)
15. 1,5-Hexafluoro-2,4-Pentanone—Tetraethylenepentamine Copolymer (1:1) (MC346).

E. Di-(2-methyl-4-aminomethyl-1,3-dioxolane)-1,4-benzene-Glutaric Dialdehyde Copolymer (MC352): To a solution of di-(2-methyl-4-aminomethyl-1,3-dioxolane)-1,4-benzene (23 mg, 75 μmol) in dimethylformamide (200 μL) was added glutaric dialdehyde (7.5 mg, 75 μmol, Aldrich Chemical Company). The reaction mixture was heated at 80° C. for 6 h under nitrogen. The solution was cooled to RT and used without further purification.

F. Di-(2-methy-4-hydroxymethyl(glycine ester)-1,3-dioxolane)-1,4,benzene—Glutaric Dialdehyde Copolymer (MC357): To a solution of di-(2-methy-4-hydroxymethyl (glycine ester)-1,3-dioxolane)-1,4,benzene (35 mg, 82 μmol) in dimethylformamide (250 μL) was added glutaric dialdehyde (8.2 mg, 82 μmol, Aldrich Chemical Company). The reaction mixture was heated at 80° C. for 12 h. The solution was cooled to RT and used without further purification.

G. Silyl Ether from Polyvinylalcohol and 3-Aminopropyltrimethoxysilane (MC221) pH-labile polyampholyte: To a solution of polyvinylalcohol (520 mg, 11.8 mmol (OH), 30,000–70,000 MW, Sigma Chemical Company) in dimethylformamide (4 mL) was added 3-aminopropyltrimethoxysilane (1.03 mL, 5.9 mmol, Aldrich Chemical Company) and the solution was stirred at RT. By similar methods the following polymers were constructed:

1. Silyl Ether from Poly-L-Arginine/-L-Serine(3:1) and 3-Aminopropyltrimethoxysilane (2:1) (MC358). Poly-L-Arginine/-L-Serine (20,000–50,000 MW, Sigma)
2. Silyl Ether from Poly-D,L-Serine and 3-Aminopropyltrimethoxysilane (3:1) (MC366). Poly-D,L-Serine (5,000–15,000 MW)
3. Silyl Ether from Poly-D,L-Serine and 3-Aminopropyltrimethoxysilane (2:1) (MC367). Poly-D,L-Serine (5,000–15,000 MW)
4. Silyl Ether from Poly-D,L-Serine and N-[3-(Triethoxysilyl)propyl]-4,5-dihydroimidizole (3:1) (MC369). Poly-D,L-Serine (5,000–15,000 MW)
5. Silyl Ether from Poly-D,L-Serine and N-Trimethoxysilylpropyl-N,N,N-trimethylammonium chloride (3:1) (MC370). Poly-D,L-Serine (5,000–15,000 MW)

6. Silazane from Poly-L-Lysine and 3-Aminopropyltrimethoxysilane (2:1) (MC360).

7. Poly(1,1-Dimethylsilazane) Tolemer (MC222).

H. 5,5'-Dithiobis(2-nitrobenzoic acid)-1,4-Bis(3-aminopropyl)piperazine Copolymer: 1,4-Bis(3-aminopropyl)piperazine (10 mL, 0.050 mmol, Aldrich Chemical Company) was taken up in 1.0 mL methanol and HCl (2 mL, 1 M in $Et_2O$, Aldrich Chemical Company) was added. $Et_2O$ was added and the resulting HCl salt was collected by filtration. The salt was taken up in 1 mL DMF and 5,5'-dithiobis[succinimidyl(2-nitro-benzoate)] (30 mg, 0.050 mmol) was added. The resulting solution was heated to 80° C. and diisopropylethylamine (35 mL, 0.20 mmol, Aldrich Chemical Company) was added by drops. After 16 h, the solution was cooled, diluted with 3 mL $H_2O$, and dialyzed in 12,000–14,000 MW cutoff tubing against water (2×2 L) for 24 h. The solution was then removed from dialysis tubing and dried by lyophilization to yield 23 mg (82%) of 5,5'-dithiobis(2-nitrobenzoic acid)-1,4-bis(3-aminopropyl)piperazine copolymer.

I. Cysteine-modified polycations: The N-hydoxysuccinimide (NHS) ester of N-Fmoc-S-tert-butylthio-L-cysteine was generated by reaction of protected amino acid with dicyclohexylcarbodiimide (DCC) and NHS in acetonitrile. After 16 h, the dicyclohexyl-urea is filtered off. The polycation is dissolved in methanol, ca 10 mg/ml, by the addition of 1 equivalent of diisopropylethylamine. To this polycation solution is added the NHS ester in acetonitrile. After 1 h, the modified polycation is precipitated out by the addition of ethyl ether. The modified polycation is then dissolved in piperidine and methanol (50/50). After 30 minutes, the cysteine-modified polycation is precipitated out by the addition of ethyl ether and then dissolved to 10 mg/ml in water. The pH of the solution is then reduced by the addition of concentrated hydrochloric acid to reduce the pH to 2.

J. Amine-containing enol ether copolymers (i.e. Poly(alkyl enolether-co-vinyloxy ethylamine) Polymers: 2-(vinyloxy)ethyl phthalimide (ImVE) was prepared by reacting 2-chloroethyl vinyl ether (25 g, 0.24 mol) with potassium phthalimide (25 g, 0.135 mol) in dimethyl foramide (75 mL) using tetra-n-butyl ammonium bromide as a phase transfer catalyst. This reaction mixture was stirred at 100° C. for 6 h then poured into 800 mL distilled water, and filtered and washed with a large amount of distilled water. The recovered yellowish crystals where then recrystallized twice from methanol to give white crystals, which were then dried for 48 h under reduced pressure. Polymerization was carried out in anhydrous methylene chloride at −78° C. under a blanket of dry nitrogen gas in oven-dried glassware. The reaction was initiated by adding borontrifluoride diethyl etherate to ImVE, and a mixture of enol ethers. The reaction was allowed to run for 3 h at −78° C., and then allowed to warm for ten minutes at RT, and then quenched with prechilled ammonia saturated methanol. The product was then evaporated to dryness under reduced pressure to give the product polymers. The polymer was then dissolved in a 1,4-dioxane (2)/methanol mixture and 10 equivalents (eq.) of hydrazine hydrate per mole of amine present. This solution was then refluxed for 2 h, cooled to RT, and the solvent was then removed under reduced pressure. This solution was then brought up in 0.5M HCl, and refluxed for 60-minutes. The cooled solution was then transferred to 3,000 MW dialysis tubing and dialyzed (4×5 L) for 48 h. This solution was then frozen and lyophilized. The following polymers were generated using this procedure:

Formulations for Amine-containing Enol Ether Copolymers

| Polymer | BF$_3$EtOEt | ImVE | octadecyl enol ether | ethyl enol ether | butyl enol ether |
|---|---|---|---|---|---|
| DW#291 | 2% | 0.875 | 0.03 | 0.095 | — |
| DW#301 | 2% | 0.75 | 0.03 | — | 0.22 |
| DW#290 | 2% | 0.97 | 0.03 | — | — |

K. Poly(alkyl enolether-co-vinyloxy ethylamine) graft lactobionic acid polycation (DW#297): DW#290 (15,000 MW) was dissolved to 50 mg/mL in 100 mM MES (pH 6.5) buffer in a 15-ml polypropylene tube. To this solution was added 0.3 molar equivalent (relative to amine content of DW#290) lactobionic acid. N-(3-Dimethylaminopropyl)-N'-ethylcarbodiimide (EDC) (0.33 equivalent) and N-hydroxysuccinimide (0.33 equivalent) were dissolved in 2 ml MES buffer and added immediately to the solution containing DW#290. The reaction tube was sealed and allowed to react at RT for 24 h. The reaction mixture was then removed from the tube and placed into dialysis tubing (3,500 MW cutoff), and dialyzed against 7×4 L water over a one week period. The polymer was then removed from the tubing and concentrated by lyophilization to 10 mg/mL.

Example 16

Demonstration of Lability of Labile Polyampholytes and Components

A. DM-poly-L-lysine: Dimethyl maleamic modified poly-L-lysine (10 mg/mL) was incubated in 10 mM sodium acetate buffer pH 5. At various times, aliquots (10 μg) were removed and added to 0.5 mL of 100 mM borax solution containing 0.4 mM trinitrobenzenesulfonate (TNBS). After 30 min, the absorbance of the solution at 420 nm was measured. To determine the concentration of amines at each time point, the extinction coefficient was determined for the product of TNBS and poly-L-lysine. Using this extinction coefficient we were able to calculate the amount of amines and maleamic groups at each time point. A plot of in ($A_t/A_0$) as a function of time was a straight line whose slope was the negative of the rate constant for the conversion of maleamic acid to amine and anhydride, where $A_t$ is the concentration of maleamic acid at a time t and $A_0$ is the initial concentration of maleamic acid. For two separate experiments we calculated rate constants of 0.066 sec$^{-1}$ and 0.157 sec$^{-1}$ which correspond to half lives of roughly 10 and 4 minutes, respectively.

B. DM-KL$_3$: Dimethyl maleamic modified KL$_3$ (0.1 mg/mL) was incubated in 40 mM sodium acetate buffer pH 5 and 1 mM cetyltrimetylammonium bromide. At various times, 10 μg aliquots were removed and added to 0.05 mL 1 M borax solution containing 4 mM TNBS. After 30 min, the absorbance of the solution at 420 nm was measured. To determine the concentration of amines at each time point, the extinction coefficient was determine for the product of TNBS and KL$_3$. Using this extinction coefficient we were able to calculate the amount of amines and maleamic groups at each time point. A plot of in ($A_t/A_0$) as a function of time was a straight line whose slope is the negative of the rate constant for the conversion of maleamic acid to amine and anhydride, where $A_t$ is the concentration of maleamic acid at a time t and $A_0$ is the initial concentration of maleamic acid. We calculated a rate constant of 0.087 $sec^{-1}$ that corresponds to a half-life of roughly 8 minutes.

C. Membrane active compounds Melittin and $KL_3$ and their dimethylmaleamic acid derivatives: The membrane-disruptive activity of the peptide melittin and subsequent blocking of activity by anionic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 μL of this suspension was used for each tube. This yields $10^8$ RBCs per tube. Each tube contained 800 μL of buffer, 200 μL of the RBC suspension, and the peptide with or without polymer. Each sample was then repeated to verify reproducibility. The tubes were incubated for 30 minutes in a 37° C. water bath. They were spun for 5 min at full speed in the microcentrifuge. Lysis was determined by measuring the absorbance of the supernatant at 541 nm, reflecting the amount of hemoglobin that had been released into the supernatant. Percent hemolysis was calculated assuming 100% lysis to be measured by the hemoglobin released by the red blood cells in water; controls of RBCs in buffer with no peptide were also run. The results, shown in the table below, indicate that dimethylmaleamic modification of the peptides $KL_3$ and Melittin inhibits their activity in a pH dependent manner. Activity of these membrane active compounds is regenerated at acidic pH.

pH-dependent Activation of Dimethylmaleamic-modified Membrane Active Polycations

| | Percent Hemolysis | |
|---|---|---|
| Peptide | pH 5.4 | pH 7.5 |
| $KL_3$ | 83 | 62 |
| DM-$KL_3$ | 37 | 4.3 |
| Succinyl-$KL_3$ | 2.0 | 1.3 |
| Melittin | 85 | 92 |
| DM-Melittin | 100 | 1.0 |
| Succinyl-Melittin | 5.0 | 2.0 |

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for enhancing delivery of a polynucleotide into a cell, comprising:
   a) forming a complex of polyampholyte containing a cleavable bond, wherein said bond is cleavable by a decrease in pH, and the polynucleotide; and,
   b) delivering the complex to a cell.

2. The process of claim 1 wherein the polyampholyte contains maleamic acid.

3. The process of claim 1 wherein the polyampholyte is membrane-disruptive upon cleavage.

4. The process of claim 1 wherein the polynucleotide is delivered to a cell in vivo.

5. The process of claim 1 wherein the polynucleotide comprises an siRNA.

6. The process of claim 1 wherein the polynucleotide comprises an expression cassette encoding an siRNA.

7. The process of claim 1 wherein the polyampholyte comprises one or more polynucleotides covalently linked to a polycation.

8. The process of claim 7 wherein the polynucleotide is linked to the polycation via a labile linkage.

9. The process of claim 8 wherein the labile linkage consists of a disulfide bond.

10. The process of claim 7 wherein the polynucleotide comprises an siRNA.

11. A complex for delivering a polynucleotide to a cell, comprising: the polynucleotide and a cleavable polyampholyte wherein the polyion and the cleavable polyampholyte are bound in complex.

12. The complex of claim 11 wherein the cleavable polyampholyte contains maleamic acid.

13. The complex of claim 11 wherein the cleavable polyampholyte is membrane-disruptive upon cleavage.

14. The complex of claim 11 wherein the polynucleotide comprises an siRNA.

15. A composition for delivering a polyion to a cell comprising: the polyion linked to a second polyion of opposite charge to form a polyampholyte.

16. The composition of claim 15 wherein the linkage consists of a labile linkage.

17. The composition of claim 16 wherein the labile linkage consists of a disulfide bond.

18. The composition of claim 16 wherein the labile linkage consists of a bond that is cleavable by a decrease in pH.

19. The composition of claim 15 where the polyion consists of a polynucleotide.

20. The composition of claim 19 where the polynucleotide consists of an siRNA.

* * * * *

```
SEQUENCE LISTING

<160> NUMBER OF SEQ ID NOS: 4

<210> SEQ ID NO 1
<211> LENGTH: 21
<212> TYPE: DNA
<213> ORGANISM: Photinus pyralis

<400> SEQUENCE: 1
cuuacgcuga guacuucgat t                                              21

<210> SEQ ID NO 2
<211> LENGTH: 21
<212> TYPE: DNA
<213> ORGANISM: Photinus pyralis

<400> SEQUENCE: 2
ucgaaguacu cagcguaagt t                                              21

<210> SEQ ID NO 3
<211> LENGTH: 8
<212> TYPE: PRT
<213> ORGANISM: Artificial
<220> FEATURE:
<223> OTHER INFORMATION: polyglutamate synthetic peptide

<400> SEQUENCE: 3

Glu Glu Glu Glu Glu Glu Glu Glu
1               5

<210> SEQ ID NO 4
<211> LENGTH: 21
<212> TYPE: PRT
<213> ORGANISM: Artificial
<220> FEATURE:
<223> OTHER INFORMATION: amphipathic synthetic peptide
```

-continued

```
<400> SEQUENCE: 4

Lys Leu Leu Lys Leu Leu Leu Lys Leu Trp Leu Lys Leu Leu Lys Leu
1               5                   10                  15

Leu Leu Lys Leu Leu
            20
```